(12) United States Patent  (10) Patent No.: US 8,496,692 B2
Bhatnagar et al.  (45) Date of Patent: Jul. 30, 2013

(54) LOCKING SECURING MEMBER

(75) Inventors: Mohit K. Bhatnagar, Potomac, MD (US); Jack Y. Yeh, North Potomac, MD (US); James A. Sack, Elverson, PA (US)

(73) Assignee: JMEA Corporation, Rockville, MD (US)

( * ) Notice: Subject to any disclaimer, the term of this patent is extended or adjusted under 35 U.S.C. 154(b) by 615 days.

(21) Appl. No.: 12/563,949

(22) Filed: Sep. 21, 2009

(65) Prior Publication Data

US 2011/0071575 A1    Mar. 24, 2011

(51) Int. Cl.
  *A61B 17/80*    (2006.01)
(52) U.S. Cl.
  USPC ........................................................ 606/289
(58) Field of Classification Search
  USPC .................. 606/280–299, 305–308; 411/141, 411/116, 979, 166
  See application file for complete search history.

(56) References Cited

U.S. PATENT DOCUMENTS

| | | |
|---|---|---|
| 864,558 A | 8/1907 | Richter |
| 3,494,243 A | 2/1970 | Kleinhenn |
| 3,672,053 A | 6/1972 | Wiss |
| 3,913,197 A | 10/1975 | Wolf |
| 4,175,555 A | 11/1979 | Herbert |
| 4,288,902 A | 9/1981 | Franz |
| 4,463,753 A | 8/1984 | Gustilo |
| 4,484,570 A | 11/1984 | Sutter et al. |
| 4,779,326 A | 10/1988 | Ichikawa |
| 4,812,095 A | 3/1989 | Piacenti et al. |
| 5,259,398 A | 11/1993 | Vrespa |
| 5,275,601 A | 1/1994 | Gogolewski et al. |
| 5,360,452 A | 11/1994 | Engelhardt et al. |
| 5,375,956 A | 12/1994 | Pennig |
| 5,387,102 A | 2/1995 | Wagner et al. |
| 5,456,719 A | 10/1995 | Keller |
| 5,536,127 A | 7/1996 | Pennig |
| 5,578,034 A | 11/1996 | Estes |
| 5,601,553 A | 2/1997 | Trebing et al. |
| 5,601,558 A | 2/1997 | Torrie et al. |
| 5,607,426 A | 3/1997 | Ralph et al. |
| 5,607,428 A | 3/1997 | Lin |
| 5,743,691 A | 4/1998 | Donovan |
| 5,904,683 A | 5/1999 | Pohndorf et al. |
| 6,030,162 A | 2/2000 | Huebner |
| 6,030,389 A | 2/2000 | Wagner et al. |
| 6,117,173 A | 9/2000 | Taddia et al. |
| 6,155,754 A | 12/2000 | Jonsson |
| 6,227,782 B1* | 5/2001 | Bowling et al. ............... 411/114 |
| 6,235,033 B1 | 5/2001 | Brace et al. |
| 6,241,731 B1 | 6/2001 | Fiz |
| 6,261,291 B1* | 7/2001 | Talaber et al. ............... 606/281 |

(Continued)

FOREIGN PATENT DOCUMENTS

WO    WO2006099766    9/2006

*Primary Examiner* — Andrew Yang
*Assistant Examiner* — Diana S Jones
(74) *Attorney, Agent, or Firm* — Plumsea Law Group, LLC

(57) ABSTRACT

An implant system is disclosed. The implant system includes a securing member configured to fasten an implant to a bone. The securing member includes a drive receiving portion with at least two deflecting portions that are configured to undergo inward deflection during insertion of the securing member into a securing hole of the implant. The deflecting portions also include locking protrusions that are configured to engage locking recesses on an outer rim of the securing hole.

22 Claims, 24 Drawing Sheets

U.S. PATENT DOCUMENTS

| | | |
|---|---|---|
| 6,322,562 B1 | 11/2001 | Wolter |
| 6,350,094 B1 | 2/2002 | Shiokawa et al. |
| 6,364,587 B1 | 4/2002 | Ingvarsson |
| 6,383,186 B1 | 5/2002 | Michelson |
| 6,506,191 B1 | 1/2003 | Joos |
| 6,575,975 B2 | 6/2003 | Brace et al. |
| 6,602,255 B1 | 8/2003 | Campbell et al. |
| 6,623,226 B2 | 9/2003 | Braun et al. |
| 6,623,486 B1 | 9/2003 | Weaver et al. |
| 6,669,701 B2 | 12/2003 | Steiner et al. |
| 6,682,533 B1 | 1/2004 | Dinsdale et al. |
| 6,719,759 B2 | 4/2004 | Wagner et al. |
| 6,726,689 B2 | 4/2004 | Jackson |
| 6,730,091 B1 | 5/2004 | Pfefferle et al. |
| 6,733,502 B2 | 5/2004 | Altarac et al. |
| 6,767,351 B2 | 7/2004 | Orbay et al. |
| 6,821,278 B2 | 11/2004 | Frigg et al. |
| 6,893,444 B2 | 5/2005 | Orbay |
| 6,902,567 B2 | 6/2005 | Del Medico |
| 6,945,975 B2 | 9/2005 | Dalton |
| 6,955,677 B2 | 10/2005 | Dahners |
| 6,960,211 B1 | 11/2005 | Pfefferle et al. |
| 6,964,664 B2 | 11/2005 | Freid et al. |
| 6,979,334 B2 | 12/2005 | Dalton |
| 6,989,013 B2 | 1/2006 | Pisharodi |
| 7,001,389 B1 | 2/2006 | Navarro et al. |
| 7,052,499 B2 | 5/2006 | Steger et al. |
| 7,063,701 B2 | 6/2006 | Michelson |
| 7,063,702 B2 | 6/2006 | Michelson |
| 7,070,599 B2 | 7/2006 | Paul |
| 7,094,239 B1 | 8/2006 | Michelson |
| 7,137,987 B2 | 11/2006 | Patterson et al. |
| 7,179,260 B2 | 2/2007 | Gerlach et al. |
| 7,204,837 B2 | 4/2007 | Paul |
| 7,250,053 B2 | 7/2007 | Orbay |
| 7,273,481 B2 | 9/2007 | Lombardo et al. |
| 7,282,053 B2 | 10/2007 | Orbay |
| 2002/0058939 A1 | 5/2002 | Wagner et al. |
| 2003/0105462 A1* | 6/2003 | Haider ............ 606/69 |
| 2003/0187443 A1 | 10/2003 | Lauryssen et al. |
| 2004/0087951 A1 | 5/2004 | Khalili |
| 2004/0127897 A1 | 7/2004 | Freid et al. |
| 2004/0193155 A1 | 9/2004 | Castaneda |
| 2005/0033298 A1 | 2/2005 | Hawkes et al. |
| 2005/0059970 A1 | 3/2005 | Kolb |
| 2005/0065524 A1 | 3/2005 | Orbay |
| 2005/0090825 A1 | 4/2005 | Pfefferle et al. |
| 2005/0096657 A1* | 5/2005 | Autericque et al. ......... 606/69 |
| 2005/0107796 A1 | 5/2005 | Gerlach et al. |
| 2005/0131413 A1 | 6/2005 | O'Driscoll et al. |
| 2005/0165400 A1 | 7/2005 | Fernandez |
| 2005/0182404 A1 | 8/2005 | Lauryssen et al. |
| 2005/0182408 A1 | 8/2005 | Pfefferle et al. |
| 2005/0187551 A1 | 8/2005 | Orbay et al. |
| 2005/0192580 A1 | 9/2005 | Dalton |
| 2005/0234456 A1 | 10/2005 | Malandain |
| 2005/0261688 A1 | 11/2005 | Grady, Jr. et al. |
| 2005/0267474 A1 | 12/2005 | Dalton |
| 2005/0277937 A1 | 12/2005 | Leung et al. |
| 2005/0283152 A1 | 12/2005 | Lindemann et al. |
| 2006/0009770 A1 | 1/2006 | Speirs et al. |
| 2006/0009771 A1 | 1/2006 | Orbay et al. |
| 2006/0015104 A1 | 1/2006 | Dalton |
| 2006/0058797 A1 | 3/2006 | Mathieu et al. |
| 2006/0089648 A1 | 4/2006 | Masini |
| 2006/0100626 A1 | 5/2006 | Rathbun et al. |
| 2006/0116678 A1 | 6/2006 | Impellizzeri |
| 2006/0149256 A1 | 7/2006 | Wagner et al. |
| 2006/0149265 A1 | 7/2006 | James et al. |
| 2006/0165510 A1 | 7/2006 | DiStasio et al. |
| 2006/0195099 A1 | 8/2006 | Bottlang |
| 2006/0200147 A1 | 9/2006 | Ensign et al. |
| 2006/0222472 A1 | 10/2006 | Jungman et al. |
| 2006/0235399 A1 | 10/2006 | Carls et al. |
| 2006/0235403 A1 | 10/2006 | Blain |
| 2006/0241618 A1 | 10/2006 | Gasser et al. |
| 2006/0257229 A1 | 11/2006 | Bucciferro et al. |
| 2006/0264946 A1 | 11/2006 | Young |
| 2006/0264947 A1 | 11/2006 | Orbay et al. |
| 2006/0276793 A1 | 12/2006 | Berry |
| 2007/0010817 A1 | 1/2007 | de Coninck |
| 2007/0043366 A1 | 2/2007 | Pfefferle et al. |
| 2007/0055249 A1 | 3/2007 | Jensen et al. |
| 2007/0073297 A1* | 3/2007 | Reynolds ............ 606/69 |
| 2007/0088360 A1 | 4/2007 | Orbay et al. |
| 2007/0118125 A1 | 5/2007 | Orbay et al. |
| 2007/0162018 A1 | 7/2007 | Jensen et al. |
| 2007/0162019 A1 | 7/2007 | Burns et al. |
| 2007/0162020 A1 | 7/2007 | Gerlach et al. |
| 2007/0212192 A1 | 9/2007 | Shirk et al. |
| 2007/0233062 A1 | 10/2007 | Berry |
| 2007/0233116 A1 | 10/2007 | Olerud |
| 2007/0233125 A1 | 10/2007 | Wahl et al. |
| 2007/0239163 A1 | 10/2007 | Strnad et al. |
| 2009/0024170 A1* | 1/2009 | Kirschman ............ 606/280 |
| 2009/0062862 A1* | 3/2009 | Perrow et al. ............ 606/280 |

* cited by examiner

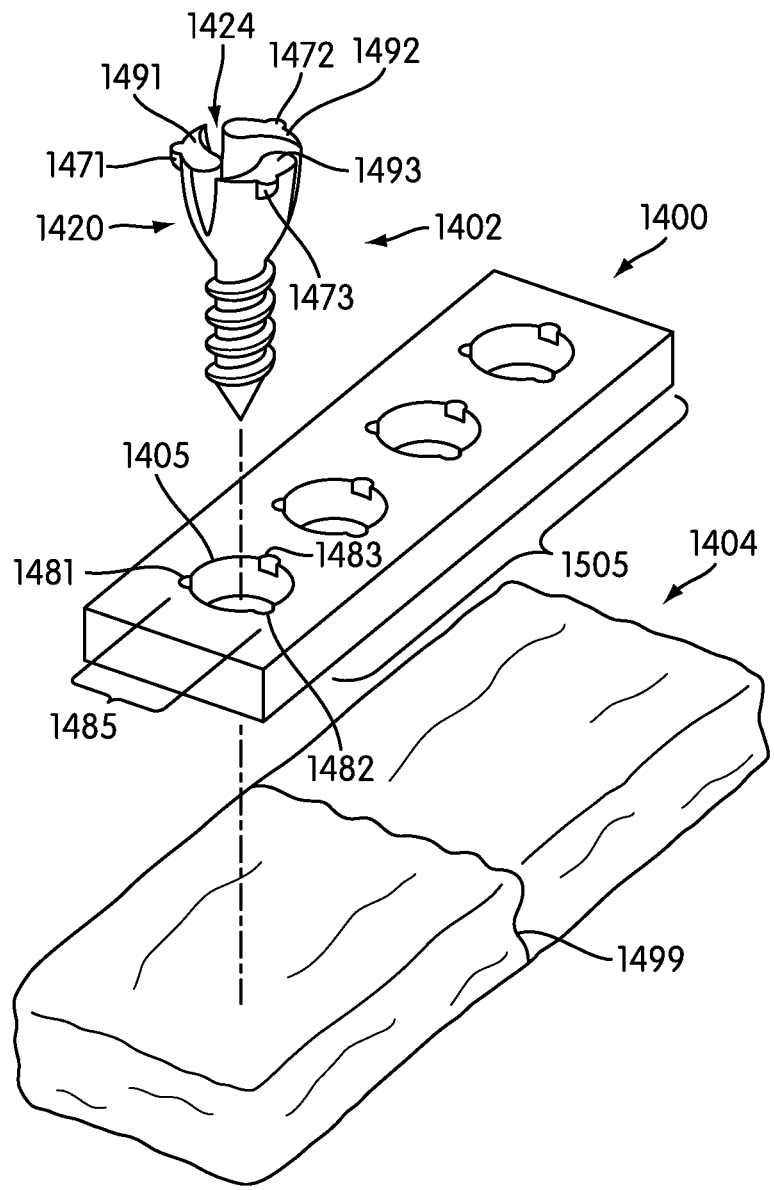
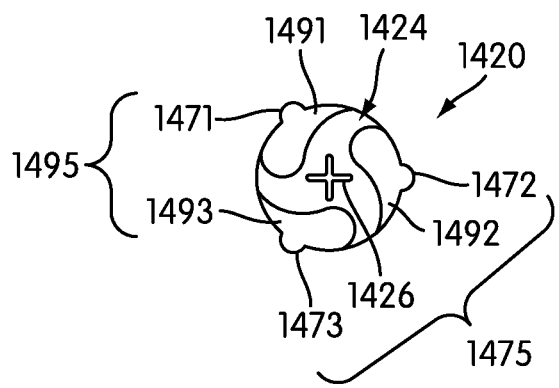
FIG. 15

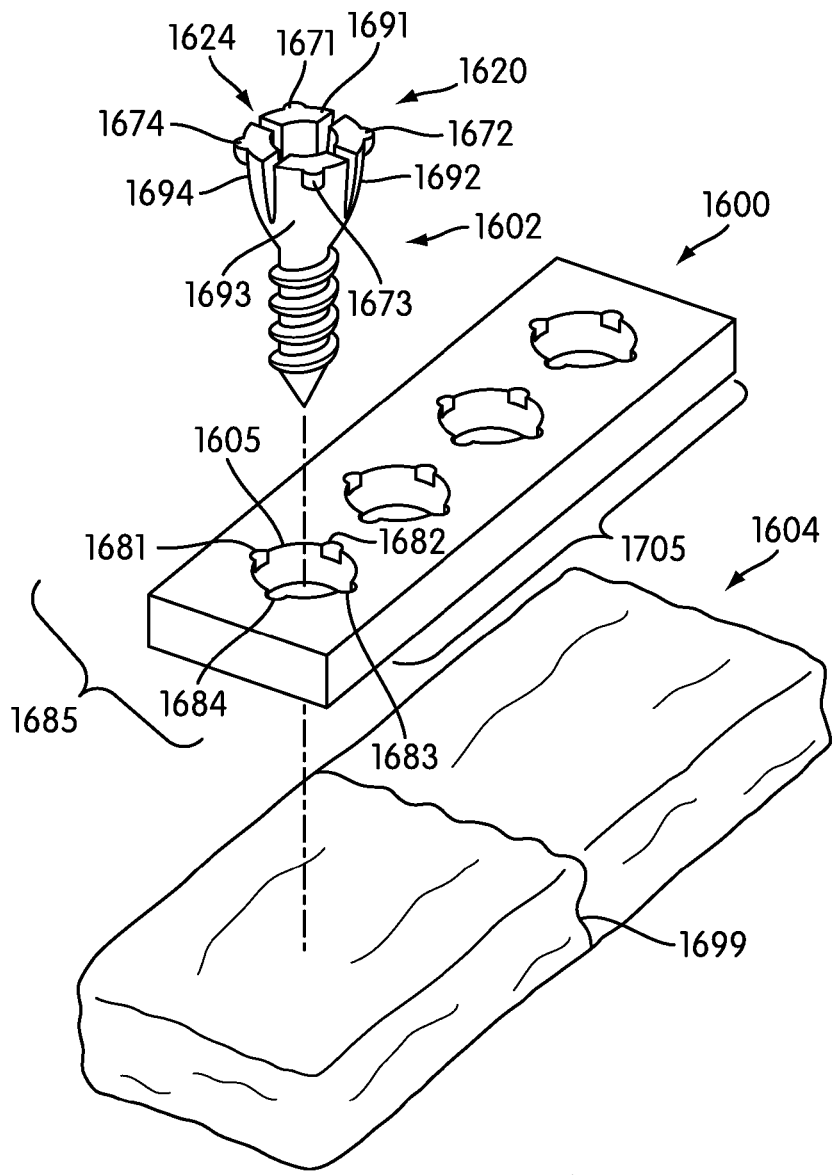
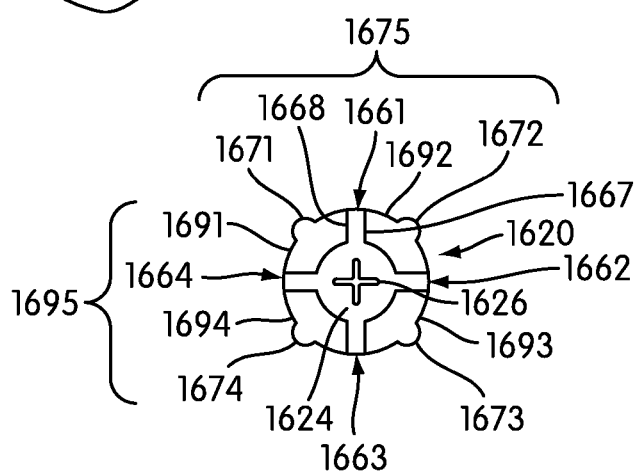
FIG. 17

LOCKING SECURING MEMBER

BACKGROUND OF THE INVENTION

1. Field of the Invention

The present invention relates generally to implantable prostheses and in particular to a securing member configured to lock into an implant.

2. Description of Related Art

Locking screws configured to implant into bone have been previously proposed. Reynolds (U.S. publication number 2007/0073297) teaches an implant with integral fastener retention. Reynolds teaches an implant to provide a simple yet effective retention system requiring no additional components beyond the implant and the associated fastener. Reynolds teaches a plurality of anti-rotation protrusions that are provided on fasteners that match recesses in an implant. As the fasteners engage the surface of the implant, protrusions engage the recesses and anti-backout surface of the recesses prevent the fastener from backing out.

The anti-rotation protrusions taught by Reynolds may engage side walls of the implant hole prior to engaging the recesses. This may lead to difficulty with inserting the screw correctly or efficiently. Furthermore, the location of the recesses makes it difficult to view the engagement of the anti-rotation protrusions with the recesses during implantation. This means that a surgeon may not know exactly when the engagement has occurred unless the surgeon attempts to rotate the screw in reverse.

Talaber (U.S. Pat. No. 6,261,291) teaches an orthopedic implant assembly. In the Talaber design, a securing element has a plurality of circumferentially spaced members. The spaced members initially deflect to fit through a collar of a transverse passageway and then expand to an uncompressed configuration by release of the radially compressive force of the collar.

Talaber teaches a securing element that is compressed and then uncompressed during implantation. This process of compressing and successively uncompressing could weaken the connection between the circumferentially spaced members and the base of the securing element.

There is a need in the art for a design that overcomes these shortcomings of the prior art.

SUMMARY OF THE INVENTION

A screw including a locking head is disclosed. In one aspect, the invention provides an implant system, comprising: a securing member configured to implant into a bone; an implant configured to associate with the bone, the implant including a securing hole for receiving the securing member; the securing member comprising a threaded portion disposed on a distal portion of the securing member and a drive receiving portion disposed on a proximal portion of the securing member; the securing member further comprising at least one deflecting portion disposed on the drive receiving portion; and where the at least one deflecting portion is configured to undergo inward deflection during insertion through the securing hole in the implant and wherein at least one deflecting portion may remain deflected following insertion.

In another aspect, the drive receiving portion has a first diameter prior to insertion and a second diameter following insertion, and wherein the second diameter is less than the first diameter.

In another aspect, the drive receiving portion has a third diameter during insertion and wherein the second diameter is different than the third diameter.

In another aspect, the securing member comprises three deflecting portions disposed on the drive receiving portion.

In another aspect, the securing member comprises four deflecting portions disposed on the drive receiving portion.

In another aspect, the at least two deflecting portions are disposed radially outwards on the drive receiving portion.

In another aspect, the drive receiving portion includes four deflecting portions and wherein each deflecting portion is separated by a slot disposed radially outwards from the center of the deflecting portion.

In another aspect, at least one deflecting portion has a shape selected from the group consisting essentially of complementary nesting shapes, segmented annulus shapes, circular shapes, rectangular shapes, triangular shapes, regular polygonal shapes and irregular shapes.

In another aspect, the invention provides an implant system, comprising: a securing member configured to implant into a bone; an implant configured to associate with the bone, the implant including a securing hole for receiving the securing member; the implant further including a first side and a second side, the second side being oriented to face the bone and the first side being oriented to face away from the bone; the securing member comprising a threaded portion on a distal portion and a drive receiving portion disposed on a proximal portion of the securing member; the securing member further comprising a first deflecting portion and a second deflecting portion disposed on the drive receiving portion; the first deflecting portion including a locking protrusion; the securing hole of the implant including a locking recess configured to receive the locking protrusion; and where the locking recess is disposed on the first side of the implant.

In another aspect, the locking recess is disposed on an upper outer rim of the securing hole.

In another aspect, a portion of the locking protrusion is disposed on a top surface of the first deflecting portion.

In another aspect, a portion of the locking protrusion is configured to be flush with the upper planar surface of the implant following insertion of the securing member.

In another aspect, the second deflecting portion includes a second locking protrusion configured to engage a second recess in the upper planar surface of the implant.

In another aspect, the invention provides an implant system, comprising: a securing member configured to implant into a bone; an implant configured to associate with the bone, the implant including a securing hole for receiving the securing member; the securing member comprising a threaded portion on a distal portion and a drive receiving portion disposed on a proximal portion of the securing member; the securing member further comprising a first deflecting portion and a second deflecting portion disposed on the drive receiving portion; and where the securing hole has a first diameter that is less than a second diameter of the drive receiving portion.

In another aspect, the securing hole is generally circular.

In another aspect, the securing hole is generally oblong to allow for pivoting of the securing member.

In another aspect, the securing hole includes a major axis and a minor axis.

In another aspect, the major axis is generally longer than the minor axis.

In another aspect, the width of the minor axis is less than the second diameter of the drive receiving portion.

In another aspect, the securing member is configured to pivot in a direction generally along the major axis.

In another aspect, the securing member is configured to pivot in a direction generally along the minor axis.

In another aspect, the first deflecting portion includes at least two locking protrusions.

In another aspect, the implant includes at least two locking recesses that are configured to receive the at least two locking protrusions.

In another aspect, the invention provides an implant system, comprising: a securing member configured to implant into a bone; an implant configured to associate with the bone, the implant including a securing hole for receiving the securing member; the implant further including a first side and a second side, the second side being oriented to face the bone and the first side being oriented to face away from the bone; the securing member comprising a threaded portion on a distal portion and a drive receiving portion disposed on a proximal portion of the securing member; the securing member further comprising a first deflecting portion and a second deflecting portion disposed on the drive receiving portion; the first deflecting portion including a locking protrusion; the securing hole of the implant including a locking recess configured to receive the locking protrusion; and where the first deflecting portion and the second deflecting portion are configured to deflect inwards during implantation of the securing member and wherein the first deflecting portion and the second deflecting portion are configured to return to a non-deflected state following implantation of the securing member.

In another aspect, the securing hole has a first diameter that is similar to a second diameter of the drive receiving portion.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 14 is an exploded isometric view of an exemplary embodiment of a securing member with three deflecting portions configured to fasten an implant to a bone;

FIG. 15 is a top view of an exemplary embodiment of a securing member with three deflecting portions;

FIG. 16 is an exploded isometric view of an exemplary embodiment of a slotted securing member with four deflecting portions that is configured to secure an implant to a bone;

FIG. 17 is a top view of an exemplary embodiment of a slotted securing member with four deflecting portions;

DETAILED DESCRIPTION OF THE PREFERRED EMBODIMENTS

Figure 1:
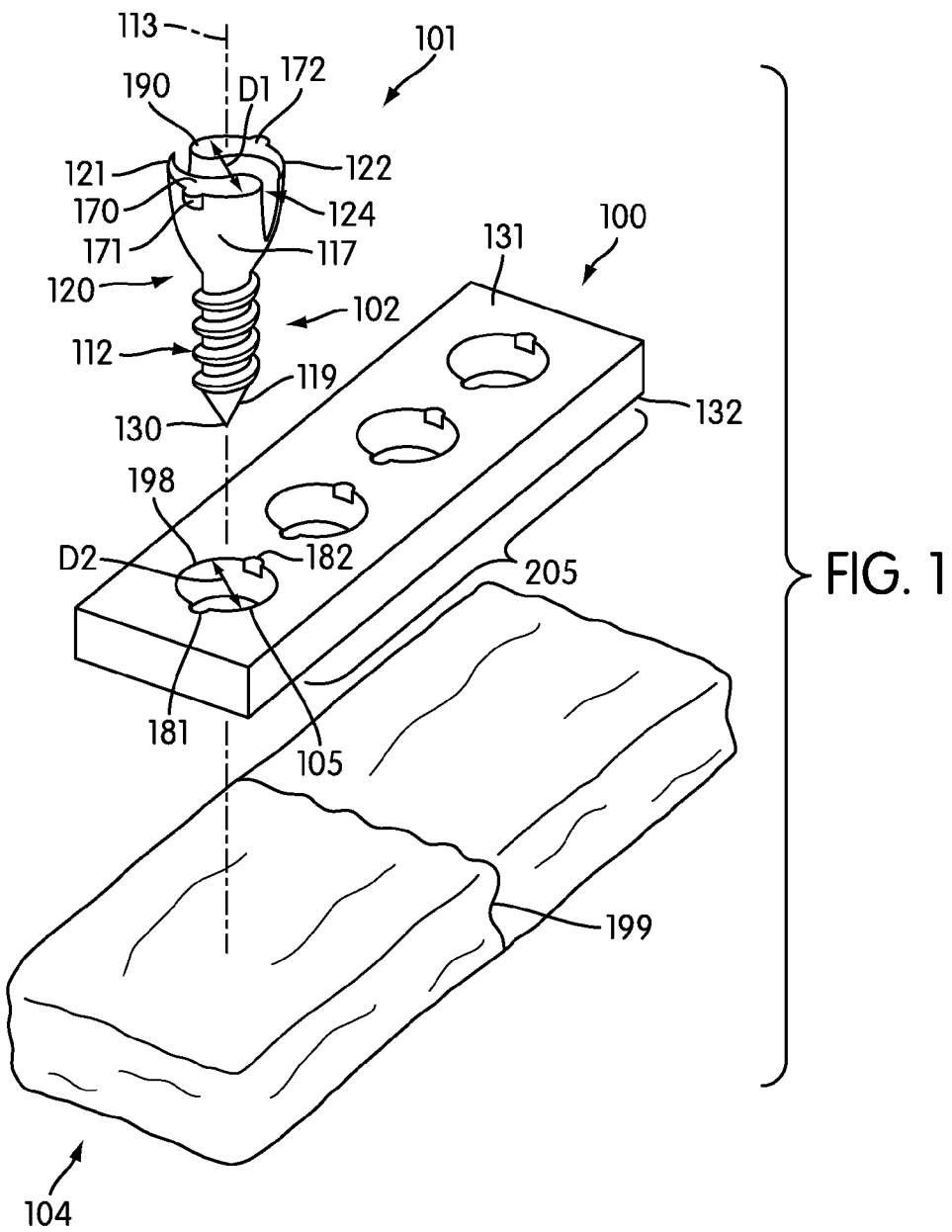
FIG. 1 is an isometric exploded view of an exemplary embodiment of a securing member configured to fasten an implant to a bone.

FIG. 1 is an exploded isometric view of an exemplary embodiment of implant system 101. In some embodiments, implant system 101 may comprise implant 100 that is associated with bone 104. Implant system 101 may also include securing member 102. Preferably, securing member 102 is configured to secure implant 100 to bone 104.

Generally, implant 100 could be any type of implant that requires the use of a securing member. Examples of different types of implants include, but are not limited to, plugs, wedges, rods, cages, connectors, wires, cables, clamps, staples, anchors or any other kind of implant. In a preferred embodiment, implant 100 is a fracture plate that is configured to facilitate healing of a fractured bone.

The term "securing member," as used throughout this detailed description and in the claims, refers to an implantable device with threading that may be configured to attach to bone. In some embodiments, a securing member may be a screw. Generally, the term securing member could refer to any type of screw, including, but not limited to, cortical screws, cancellous screws, cannulated screws, partially cannulated screw, or self tapping screws. Furthermore, a securing member may be used alone to provide internal fixation or in conjunction with other implantable prostheses.

In some cases, a securing member such as a screw may secure an implantable prosthesis to bone for reinforcement purposes. In other cases, securing members may fasten an implantable prosthesis to bone to augment healing. In still other cases, one or more securing members may be used to secure an implant to provide anatomic alignment for healing a fractured bone.

In this exemplary embodiment, securing member 102 is configured to attach implant 100 to bone 104 in order to reinforce bone 104 at fracture 199. For purposes of clarity, fracture 199 is shown as a single break in bone 104. In other embodiments, however, fracture 199 could be associated with multiple breaks or any general type of structural damage to bone 104. Furthermore, it should be understood that in other embodiments, implant system 101 could be used to facilitate healing of other types of injuries related to a bone and/or surrounding tissue. For example, in some embodiments, an implant could be used to fuse together two vertebrae following the removal of a portion of an intervertebral disc.

Generally, the shape of the implant used may vary according to the type of bone and the type of fracture requiring healing. For purposes of illustration, implant 100 is shown here as a rectangular fracture plate. However, in other embodiments, implant 100 could have any type of shape, including, but not limited to, a circular, oval, polygonal or irregular shape. Additionally, in some cases, implant 100 could be bent in one or more directions to conform to the shape of the associated bone and tissue.

Implant 100 may include provisions to facilitate implantation and healing of adjacent bone and tissue. In some embodiments, an intermediate tissue or membrane may be disposed between implant 100 and bone 104. In other words, implant 100 may not directly contact bone 104. Instead, implant 100 may be configured to contact some other tissue or membrane disposed adjacent to bone 104. This membrane can include muscle or periosteum. In other embodiments, implant 100 may include a liner. In some cases, the liner may fit into a recess disposed in implant 100. However, in other cases, no recess may be provided for the liner.

In some embodiments, implant 100 could include provisions for facilitating bone growth. In some cases, implant 100 may include holes to help induce bone growth into implant 100. In this manner, bone 104 may be partially fused to implant 100. In other cases, implant 100 may be selectively coated with a bone growth promoting agent to help stimulate bone growth. Examples of implants including holes and/or selectively applied bone growth promoting agents are disclosed in U.S. patent applications Ser. No. 11/740,181 filed on Apr. 25, 2007; U.S. patent applications Ser. No. 11/840,707 filed on Aug. 17, 2007; and U.S. patent applications Ser. No. 11/859,386 filed on Sep. 21, 2007, the entirety of which are hereby incorporated by reference.

It should be understood that similar provisions for promoting bone growth and bone fusion could also be provided on one or more portions of securing member 102. In particular, securing member 102 could also include holes for promoting ingrowth of bone. Additionally, securing member 102 could include one or more selectively applied bone growth promoting agents.

In order to facilitate the attachment of implant 100 to bone 104, implant 100 may include securing hole set 205. Generally, securing hole set 205 may include any number of holes. In this embodiment, securing hole set 205 includes four holes. In other embodiments, securing hole set 205 may include less than four holes. In still other embodiments, securing hole set 205 may include more than four holes.

Generally, securing holes may be arranged in any manner within implant 100. In some embodiments, securing holes may be configured on either side of a fracture in a bone. In the current arrangement, securing hole set 205 is arranged so that two holes of securing hole set 205 may be disposed on one side of fracture 199 and two holes of securing hole set 205 are disposed on a second side of fracture 199. In this exemplary embodiment, securing member 102 may be inserted into securing hole 105 of securing hole set 205 to fasten implant 100 to bone 104.

For this embodiment and all the following example embodiments, only a single securing member is shown for the sake of clarity. However, in all the embodiments in this detailed description it should be understood that additional securing members may be inserted and fastened into remaining holes of securing hole 205 set in a similar manner. In particular, in the preferred embodiment, these additional securing members may be similar to securing member 102.

Furthermore, while the exemplary embodiment includes securing holes of a similar size, in other embodiments the sizes of the securing holes and the associated securing members may vary. For example, in another embodiment, securing holes 205 may have different sizes and may be associated with securing members of differing sizes.

In this exemplary embodiment, implant 100 includes first side 131 and second side 132. In particular, first side 131 is disposed opposite of second side 132. When implant 100 is fastened to bone 104, second side 132 may be oriented to face bone 104. Likewise, first side 131 may be oriented to face away from bone 104. It should be understood that while first side 131 and second side 132 are generally planar in the current embodiment, in other embodiments first side 131 and/or second side 132 may be contoured in various manners.

Generally, an implant may have any thickness. In some embodiments, the implant may be thicker than a drive receiving portion of a securing member. In other embodiments, the implant may be thinner than a drive receiving portion of a securing member. In a preferred embodiment, an implant may be about as thick as a drive receiving portion of a securing member. It should be understood that the thicknesses of the implants illustrated in the following embodiments can be varied according to medically appropriate plate thicknesses based on various factors, such as pathologies, anticipated stresses, etc.

Preferably, a securing member is configured with provisions to insert and fasten the securing member to an implantable prosthesis and bone. Typically, a securing member such as a bone screw may be fastened with a fastening tool, such as a screw driver, hex key or a drill. In some embodiments, the securing member may include a drive receiving portion to receive the fastening tool.

In the current embodiment, securing member 102 includes drive receiving portion 120 disposed on proximal portion 117 of securing member 102. In some embodiments, drive receiving portion 120 may be further associated with first deflecting portion 121 and second deflecting portion 122. Preferably, first deflecting portion 121 and second deflecting portion 122 may be disposed radially outwards from central axis of drive receiving portion 120. In the preferred embodiment, first deflecting portion 121 and second deflecting portion 122 may be spaced apart from one another, forming central cavity 124 of drive receiving portion 120.

Securing member 102 may be associated with rotational axis 113. Rotational axis 113 may be disposed through the center of securing member 102 in a lengthwise direction, as seen in FIG. 1. Throughout this detailed description and in the claims, the axial direction refers to any direction parallel with rotational axis 113 of securing member 102. Likewise, the radial direction refers to any direction that intersects, and is generally perpendicular to, the axis of rotation of securing member 102.

Figure 2:
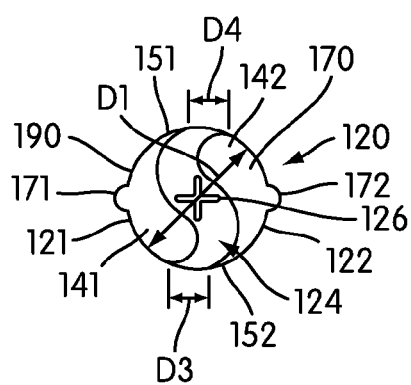
FIG. 2 is a top view of an exemplary embodiment of a securing member with two deflecting portions.

Referring to FIG. 2, drive receiving portion 120 may also include drive receiving surface 126. In this embodiment, drive receiving surface 126 is recessed with respect to top surface 170 of drive receiving portion 120. Drive receiving surface 126 may also be disposed between first deflecting portion 121 and second deflecting portion 122. With this arrangement, force from a fastening tool may be applied between first deflecting portion 121 and second deflecting portion 122, rather than directly to first deflecting portion 121 and second deflecting portion 122 in order to prevent inadvertent deflection by the fastening tool.

Generally, drive receiving surface 126 may be configured to mate with any desired fastening tool. For example, drive receiving surface 126 may include a slot, Philips, star, hex, torx, Robertson, tri-wing, torq-set, spanner head, triple square, or any other desired mechanical coupling. In this exemplary embodiment, drive receiving surface 126 includes a Philips configuration for mechanical coupling with a fastening tool. With this arrangement, drive receiving surface 126 may engage a fastening tool and allow securing member 102 to be rotated and fastened.

Referring back to FIG. 1, securing member 102 may include provisions for inserting into bone 104. In this embodiment, securing member 102 may include threaded portion 112 disposed on distal portion 119 of securing member 102. Generally, threaded portion 112 may include any type of threading including, but not limited to, single threading, multiple threading as well as helical threading. Additionally, the pitch width of the threading may have any value. Furthermore, the pitch width may be variable or constant. In this embodiment, threaded portion 112 includes a single threading with a constant pitch width.

In the current embodiment, threaded portion 112 may be further associated with tip 130. Generally, tip 130 may be a solid or hollow boring tip. In this exemplary embodiment, tip 130 is a solid boring tip that allows securing member 102 to be inserted into a region of bone 104 where no previous hole has been made. In particular, tip 130 may be inserted through securing hole 105 of implant 100 and penetrate through bone 104 as bone securing member 102 is rotated.

Preferably, an implant system includes provisions for maintaining a tight connection between a securing member and an implant following implantation. In particular, a securing member may include provisions that help resist movement of the securing member within a securing hole. In some embodiments, a securing member may include deflecting portions configured to undergo inward deflection. The term "deflection" as used throughout this detailed description and in the claims refers to the displacement of a structure. In some embodiments, this deflection can cause temporary or elastic deformation of the structure. In other words, the shape of the structure may be temporarily changed. In other embodiments, this deflection can cause permanent or plastic deformation of the structure. In other words, the shape of the structure may be permanently changed. This would be referred to as deformation. It should be understood that deflecting portions associated with a securing member can be configured for elastic and/or plastic deformation, which would be referred to generally as deflection. As the deflecting portions undergo various types of deflection and/or deformation, they may provide a tensioning force against an inner wall of a securing hole to prevent the securing member from moving.

In this embodiment, first deflecting portion 121 and second deflecting portion 122 may be configured for inward deflection when securing member 102 is inserted into implant 100. In some embodiments, this inward deflection is generally directed along the radial direction. In other embodiments, the deflection may be directed in other direction as well. For example, in some cases, first deflecting portion 121 and second deflecting portion 122 could be configured for axial and circumferential deflection as well.

In some embodiments, drive receiving portion 120 may be configured as slightly larger than securing hole 105 to provide for a tensioned or interference fit between securing member 102 and implant 100. In this exemplary embodiment, first deflecting portion 121 and second deflecting portion 122 may be initially arranged so that drive receiving portion 120 has a first diameter D1. Additionally, securing hole 105 may have a second diameter D2. In a preferred embodiment, first diameter D1 may be slightly larger than second diameter D2. With this configuration, as drive receiving portion 120 is inserted through securing hole 105 during implantation, first deflecting portion 121 and second deflecting portion 122 may undergo inward deflection to accommodate the differences in the diameters of drive receiving portion 120 and securing hole 105. In other words, first deflecting portion 121 and second deflecting portion 122 may be squeezed together as drive receiving portion 120 is wedged into securing hole 105.

Referring to FIG. 2, the shapes of first deflecting portion 121 and second deflecting portion 122 may facilitate a strengthened tension fit with securing hole 105, as first deflecting portion 121 and second deflecting portion 122 undergo inward radial deflection. In the current embodiment, first deflecting portion 121 and second deflecting portion 122 have similar shapes. First deflecting portion 121 may include first head portion 141 and first tail portion 151. Preferably, first deflecting portion 121 is wider at first head portion 141 and generally tapers towards first tail portion 151 that is much narrower than first head portion 141. Likewise, second deflecting portion 122 may include second head portion 142 and second tail portion 152. Preferably, second deflecting portion 122 is wider at second head portion 142 and generally tapers towards second tail portion 152.

First deflecting portion 121 and second deflecting portion 122 may be further arranged so that first head portion 141 of first deflecting portion 121 is disposed adjacent to second tail portion 152 of second deflecting portion 122. Likewise, second head portion 142 of second deflecting portion 122 may be disposed adjacent to first tail portion 151 of first deflecting portion 121. With this arrangement, first deflecting portion 121 and second deflecting portion 122 may present complementary nesting shapes. In this exemplary embodiment, first deflecting portion 121 and second deflecting portion 122 present "yin-yang" like shapes along top surface 170 of drive receiving portion 120. This complementary arrangement allows for a complementary fit between first deflecting portion 121 and second deflecting portion 122 as drive receiving portion 120 undergoes inward deflection.

Preferably, first deflecting portion 121 and second deflecting portion 122 are spaced apart to allow for inward deflection. As previously discussed, first deflecting portion 121 and second deflecting portion 122 are configured with first head 141 of first deflecting portion 121 proximate to second tail 152 of second deflecting portion 122. In the current embodiment, first head 141 and second tail 152 are separated by distance D3. Likewise, second head 142 of second deflecting portion 122 is disposed proximate to first tail 151 of first deflecting portion 121. In this embodiment, second head 142 and first tail 151 are separated by distance D4. Typically, distance D3 and distance D4 are approximately equal and significantly less than diameter D1 of drive receiving portion 120. With this configuration, the circumference of drive receiving portion 120 may generally decrease as first deflecting portion 121 and second deflecting portion 122 are inserted through securing hole 105. This arrangement allows drive receiving portion 120 to maintain a generally circular shape so that tension forces can be more evenly distributed between drive receiving portion 120 and inner walls of securing hole 105.

Generally, deflecting portions on a drive receiving portion of a securing member may be formed by cutting or removing portions of a drive receiving portion. In some cases, a central cavity on a drive receiving portion may also be created as the deflecting portions on a drive receiving portion are cut. This cutting may be done using techniques known in the art, such as stamping, punching, laser cutting, water drilling, electrical discharge machining (EDM), broaching, etc., or any combination of techniques. In other embodiments, deflecting portions may be formed using a die of some kind. It should be understood that these various methods for forming a deflecting portion as discussed for this two deflecting portion arrangement may also be applied to other embodiments with a different number of deflecting portions and/or different shaped deflecting portions.

In some embodiments, an implant system may include additional provisions to prevent unwanted movement of the securing member following implantation. In some cases, a securing member may include provisions for resisting reverse rotation following implantation, to prevent the securing member from backing out of the securing hole. In a preferred embodiment, a securing member may include locking protrusions that fit into corresponding locking recesses within an implant to lock the securing member into place following insertion.

Referring to FIGS. 1 and 2, securing member 102 may include first locking protrusion 171 and second locking protrusion 172. Generally, first locking protrusion 171 and second locking protrusion 172 may be disposed on any portions of drive receiving portion 120. In the exemplary embodiment, first locking protrusion 171 may be disposed on first deflecting portion 121. Additionally, second locking protrusion 172 may be disposed on second deflecting portion 122. In a preferred embodiment, first locking protrusion 171 and second locking protrusion 172 may be generally coincident with outer periphery 190 of top surface 170 of drive receiving portion 120. In other words, first locking protrusion 171 and second locking protrusion 172 may be disposed at the top of securing member 102.

Although this embodiment includes a single locking protrusion disposed on each deflecting portion of a securing member, in other embodiments, any number of locking protrusions can be disposed on a single deflecting portion. For example, in some cases, two or more locking protrusions can be disposed on a single deflecting portion of a securing member.

Generally, the location of first locking protrusion 171 and second locking protrusion 172 along outer periphery 190 of first deflecting portion 121 and second deflecting portion 122, respectively, may vary. In some embodiments, first locking protrusion 171 may be disposed adjacent to first head portion 141. In other embodiments, first locking protrusion 171 may be disposed adjacent to first tail portion 151. In a preferred embodiment, first locking protrusion 171 may be disposed mid-way between first head portion 141 and first tail portion 151, as illustrated in FIG. 2. Furthermore, in some embodiments, second locking protrusion 172 may be disposed adjacent to second head portion 142. In other embodiments, second locking protrusion 172 may be disposed adjacent to second tail portion 152. In a preferred embodiment, second locking protrusion 172 may be disposed mid-way between second head portion 142 and second tail portion 152. With this preferred embodiment, first locking protrusion 171 and second locking protrusion 172 may be spaced substantially equidistantly on outer periphery 190.

Implant 100 may include first locking recess 181 and second locking recess 182 for receiving first locking protrusion 171 and second locking protrusion 172. Generally, first locking recess 181 and second locking recess 182 may be located anywhere on implant 100. In some embodiments, first locking recess 181 and second locking recess 182 may be disposed on first side 131 of implant 100. In a preferred embodiment, first locking recess 181 and second locking recess 182 may be disposed on upper outer rim 198 of securing hole 105. The term "upper outer rim" as used throughout this detailed description and in the claims refers to a portion of a securing hole that defines an opening between the securing hole and a side of the implant facing away from a bone.

Generally, first locking recess 181 and second locking recess 182 can receive either first locking protrusion 171 or second locking protrusion 172 when securing member 102 is fastened to implant 100 and bone 104. For example, as securing member 102 is inserted through securing hole 105 and into bone 104, first locking protrusion 171 may eventually fall down into first locking recess 181. Likewise, second locking protrusion 172 may eventually fall into second locking recess 182. Preferably, the shape of first locking recess 181 and second locking recess 182 help to prevent first locking protrusion 171 and second locking protrusion 172, respectively, from escaping. With this configuration, first locking protrusion 171 and second locking protrusion 172 may resist movement that may unfasten securing member 102 from bone 104 and implant 100.

Generally, locking protrusions and locking recesses may be configured with any shapes. In some embodiments, a locking protrusion and a locking recess configured to receive the locking protrusion may be configured with complementary shapes. In some cases, the locking recess and the locking protrusions could be rounded. For example, the locking recess could be a hemispherical shaped indentation in the implant, while the locking protrusions could be a hemispherical shaped protrusion. In another example, the locking recess could have a fin like shape that presents a sloped surface on one side and a generally flat anti-backing out surface on another side. Therefore, as the locking protrusion slides into the locking recess, the generally flat anti-backing out surface provides additional resistance against reversing the fastening direction of the securing member.

FIGS. 3-8 illustrate a schematic view of an exemplary embodiment of securing member 102 fastening implant 100 to bone 104. Prior to insertion of securing member 102, implant 100 may be disposed against bone 104 at the desired region of attachment. As previously discussed, first side 131 of implant 100 may be disposed upwards, facing away from bone 104. At this point, securing member 102 may be associated with, and positioned inside of, securing hole 105.

Figure 3:
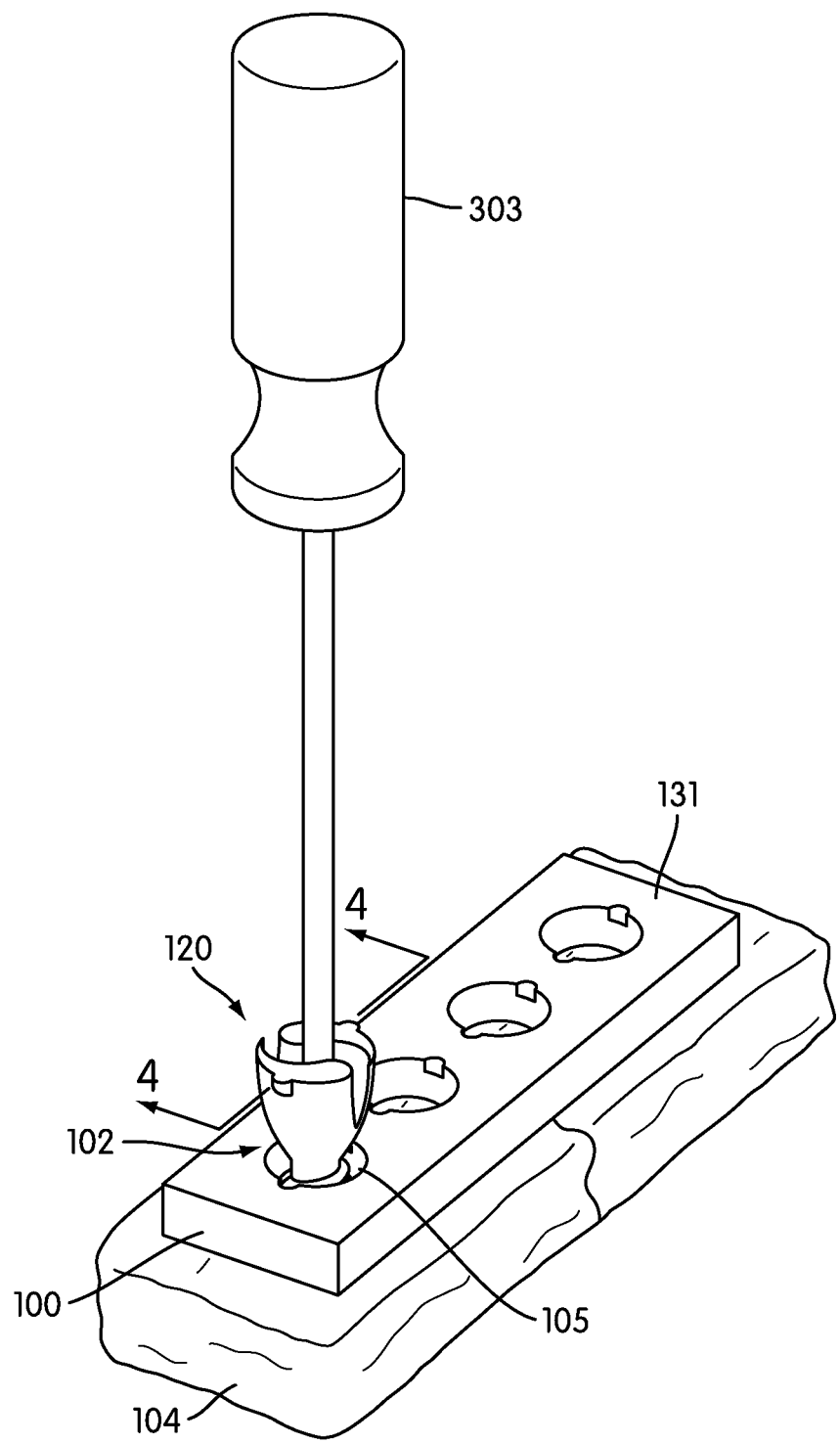
FIG. 3 is an isometric view of an exemplary embodiment of a securing member fastening an implant to a bone.
Figure 4:
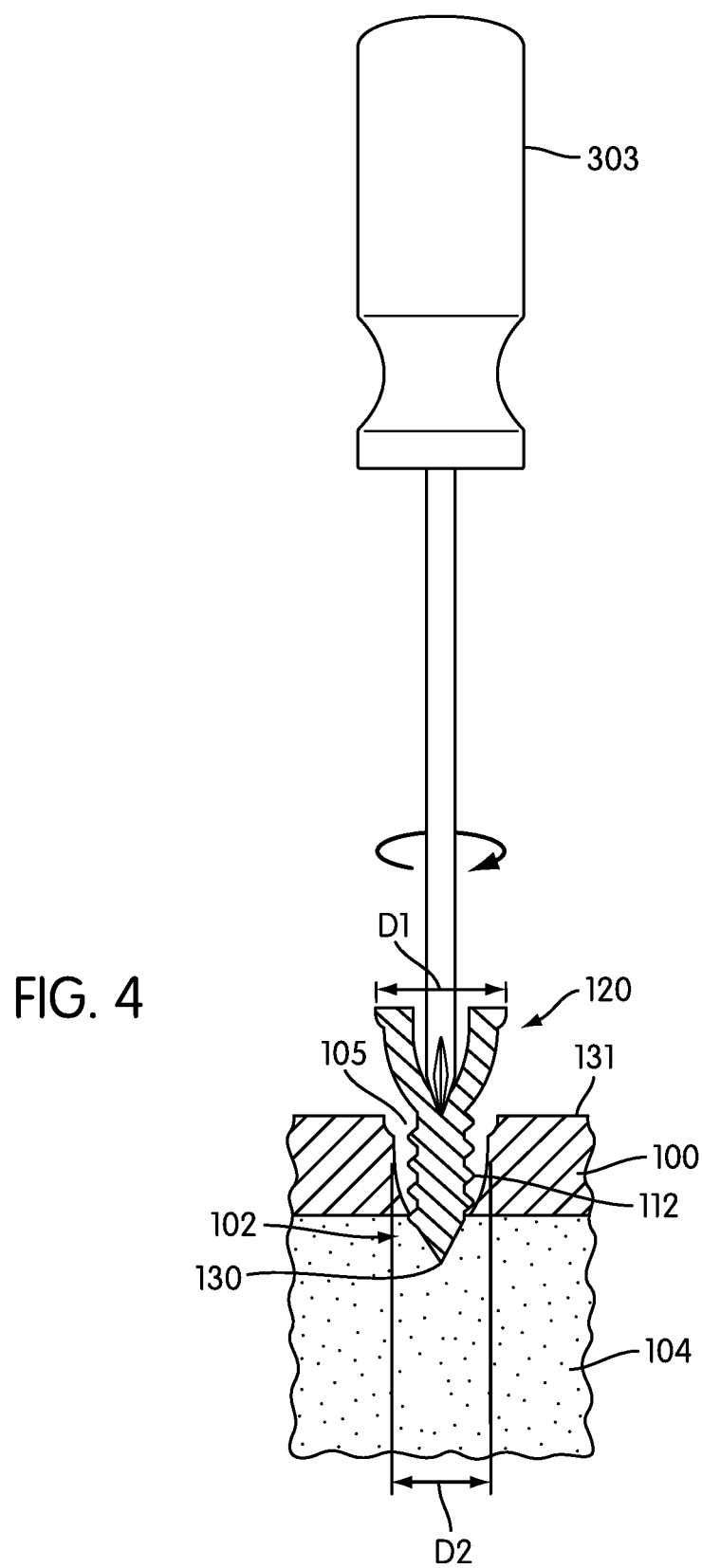
FIG. 4 is a cross sectional view of an exemplary embodiment of a securing member fastening an implant to a bone.

FIGS. 3 and 4 illustrate the initial insertion of securing member 102 through securing hole 105 of implant 100. At this point, fastening tool 303 is engaged with securing member 102 and used to drive securing member 102 partially into bone 104. Generally, fastening tool 303 may fasten securing member 102 in any manner. In this embodiment, a surgeon can turn fastening tool 303 in a clockwise direction to fasten securing member 102. As securing member 102 is rotated, tip 130 and threaded portion 112 may penetrate into bone 104.

At this point, threaded portion 112 is partially inserted into bone 104. Furthermore, drive receiving portion 120 has not been inserted through securing hole 105. Prior to insertion through securing hole 105, drive receiving portion 120 still has a first diameter D1 that is larger than second diameter D2 of securing hole 105.

As illustrated in the Figures, drive receiving portion 120 can have a contoured shape with outer walls that are sloped rather than parallel with an axial direction of securing member 120. Because the diameter of drive receiving portion 120 can taper or slope over the axial length of drive receiving portion 120, it should be understood that first diameter D1 may be associated with an average diameter of drive receiving portion 120. Likewise, throughout the remainder of this detailed description, and in the claims, any diameter associated with a securing hole 105 or drive receiving portion 120 may be an average diameter, rather than the diameter at a particular axial location.

Figure 5:
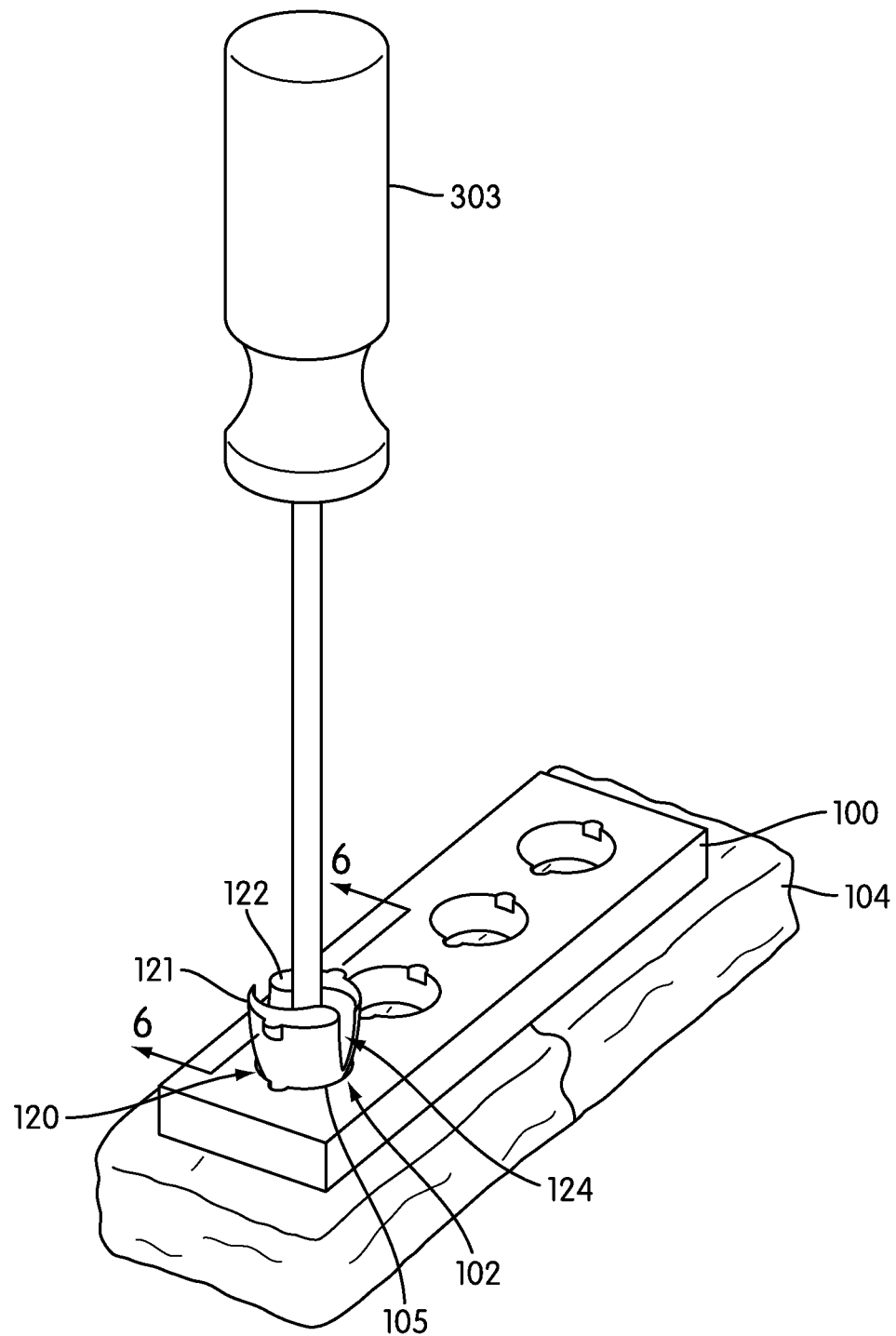
FIG. 5 is an isometric view of an exemplary embodiment of a securing member fastening an implant to a bone.
Figure 6:
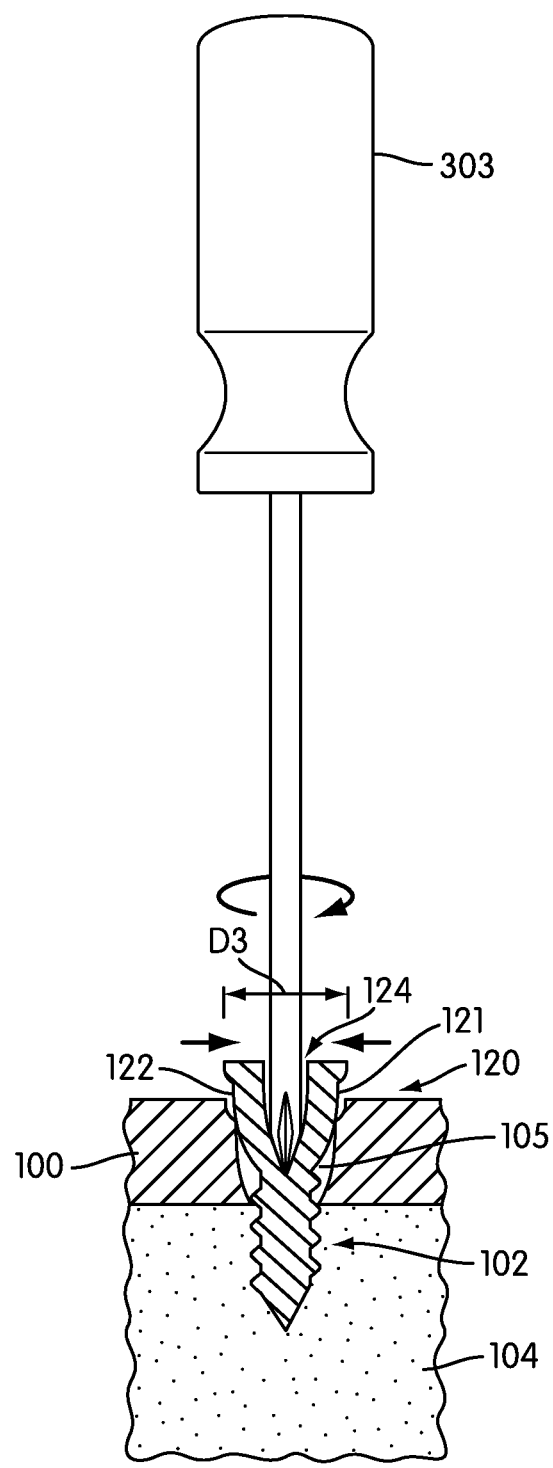
FIG. 6 is a cross sectional view of an exemplary embodiment of a securing member fastening an implant plate to a bone.

Referring to FIGS. 5 and 6, fastening tool 303 continues to fasten securing member 102 into bone 104. As securing member 102 is driven further into bone 104, drive receiving portion 120 contacts securing hole 105. As previously discussed, diameter D1 of drive receiving portion 120 is larger than diameter D2 of securing hole 105, prior to insertion of securing member 102 (see FIG. 4). Therefore, first deflecting portion 121 and second deflecting portion 122 undergo inward deflection to accommodate the difference in diameters of drive receiving portion 120 and securing hole 105 during insertion. In some cases, this deflection may also cause central cavity 124 to decrease in size. In this exemplary embodiment, drive receiving portion 120 has a third diameter D3 that is less than first diameter D1 that is associated with drive receiving portion 120 prior to insertion. As first deflecting portion 121 and second deflecting portion 122 are deflected inwards, frictional forces may increase between drive receiving portion 120 and securing hole 105 due to drive receiving portion 120 being placed in compression against the inner surface of securing hole 105. This preferably results in a tighter fit of securing member 102 in securing hole 105.

Figure 7:
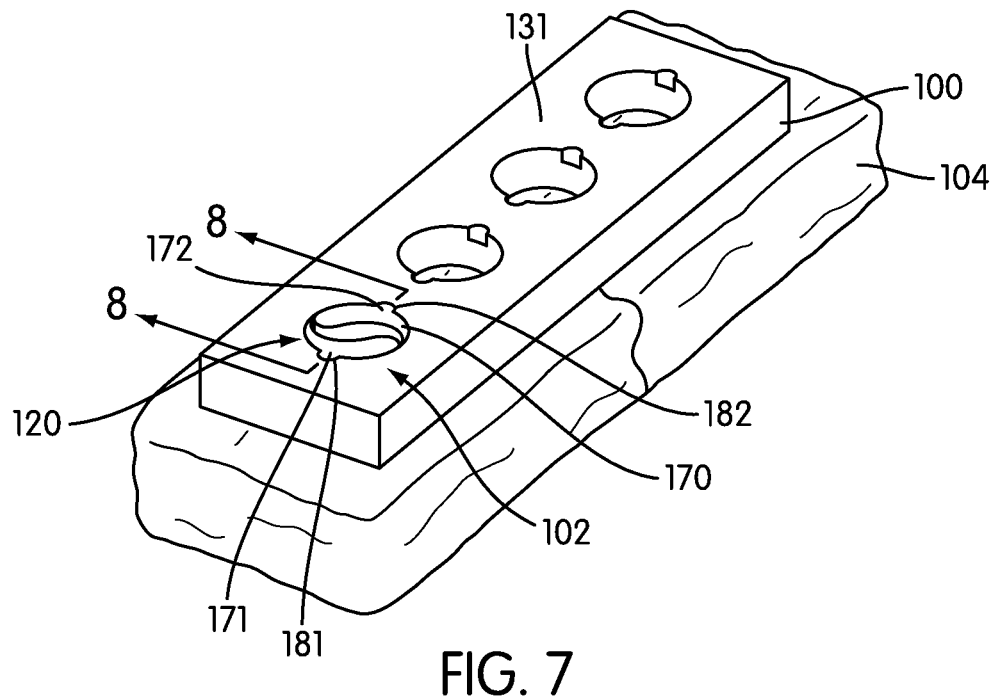
FIG. 7 is an isometric view of an exemplary embodiment of a securing member fully inserted into a implant to secure the fracture plate to a bone.
Figure 8:
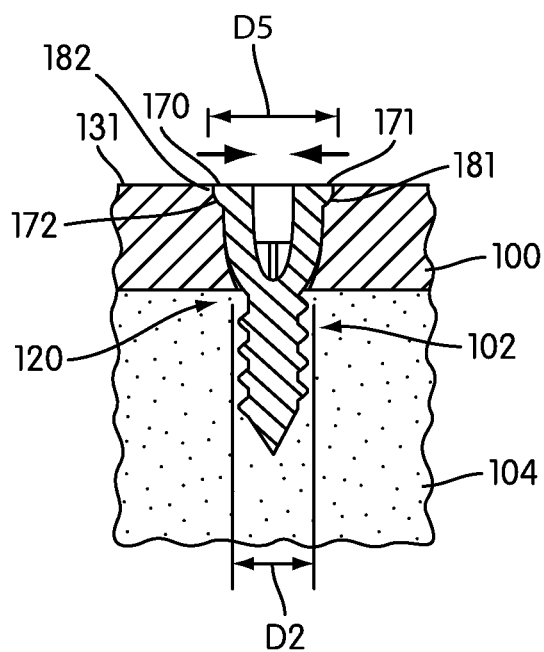
FIG. 8 is a cross sectional view of an exemplary embodiment of a securing member fully inserted into an implant to secure the implant to a bone.

Referring to FIGS. 6-8, securing member 102 is fully inserted in implant 100. Generally, securing member 102 may be fastened until first locking protrusion 171 and second locking protrusion 172 are engaged in the closest locking recess, either first locking recess 181 or second locking recess 182. In some embodiments, securing member 102 is fastened until top surface 170 of drive receiving portion 120 is generally flush with first side 131 of implant 100. In this preferred embodiment, first locking protrusion 171 and second locking protrusion 172 are fit within first locking recess 181 and second locking recess 182, respectively. In other embodiments, however, first locking protrusion 171 or second locking protrusion 172 may fit in either first locking recess 181 or second locking recess 182. With this preferred arrangement, first locking protrusion 171 and second locking protrusion 172 may prevent unwanted movement of securing member 102 within securing hole 105.

With securing member 102 fully inserted in securing hole 105, first deflecting portion 121 and second deflecting portion 122 have undergone a deflection that has resulted in permanent inward deformation. This deformation has decreased the diameter of drive receiving portion 120. Referring to FIG. 8, drive receiving portion 120 has a fifth diameter D5 in the installed state. Preferably, installed sixth diameter D5 is less than pre-installation first diameter D1 and third diameter D3 occurring during installation. Furthermore, fifth diameter D5 may be approximately equal to second diameter D2 associated with securing hole 105. This arrangement provides an increasing compressive fit between securing hole 105 and drive receiving portion 120 to prevent movement of securing member 102.

In some embodiments, first diameter D1 associated with drive receiving portion 120 may have a value similar to second diameter D2 associated with securing hole 105. With this arrangement, as drive receiving portion 120 is rotated, first deflecting portion 121 and second deflecting portion 122 may deflect inwardly as first locking protrusion 171 and second locking protrusion 172 are disposed against securing hole 105. However, as first locking protrusion 171 and second locking protrusion 172 engage first locking recess 181 and second locking recess 182, respectively, first deflecting portion 121 and second deflecting portion 122 may deflect to fit against walls of securing hole 105. In other words, first deflecting portion 121 and second deflecting portion 122 can be configured to return substantially to a pre-deflected or pre-deformed state after securing member 102 has been fastened to securing hole 105.

In some embodiments, the location of one or more locking protrusions can be varied. In some cases, a locking protrusion can be disposed on an intermediate portion of a drive receiving portion. In other cases, a locking protrusion can be disposed on a lower portion of a drive receiving portion. In other embodiments, a locking protrusion may have a rib-like shape that extends between an upper portion and a lower portion of a drive receiving portion. In still other embodiments, a securing member may not include any protrusions.

Figure 18:
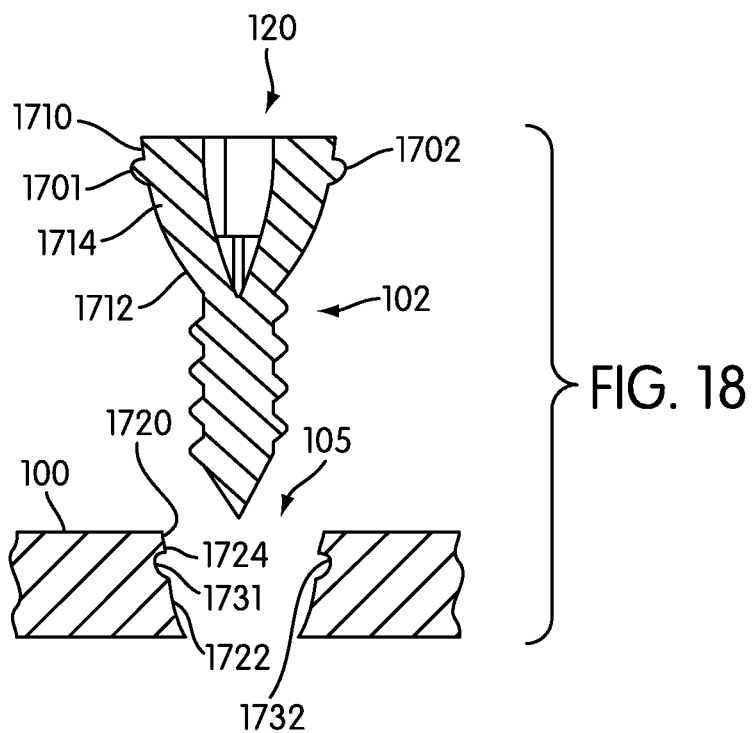
FIG. 18 is a side cross sectional view of a preferred embodiment of a securing member and an implant.
Figure 19:
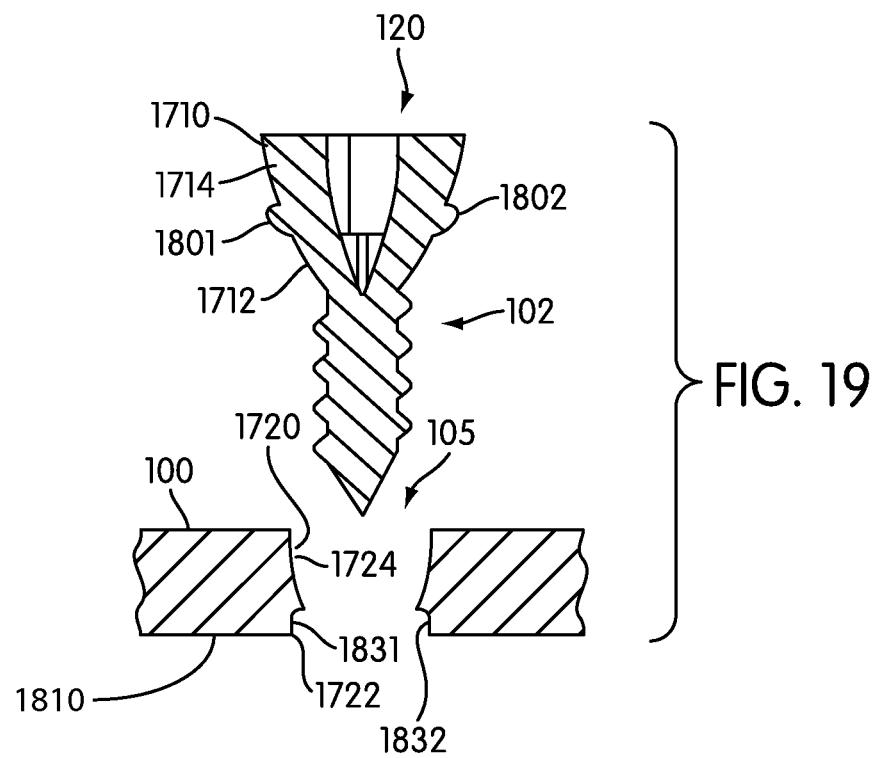
FIG. 19 is a side cross sectional view of a preferred embodiment of a securing member and an implant.
Figure 20:
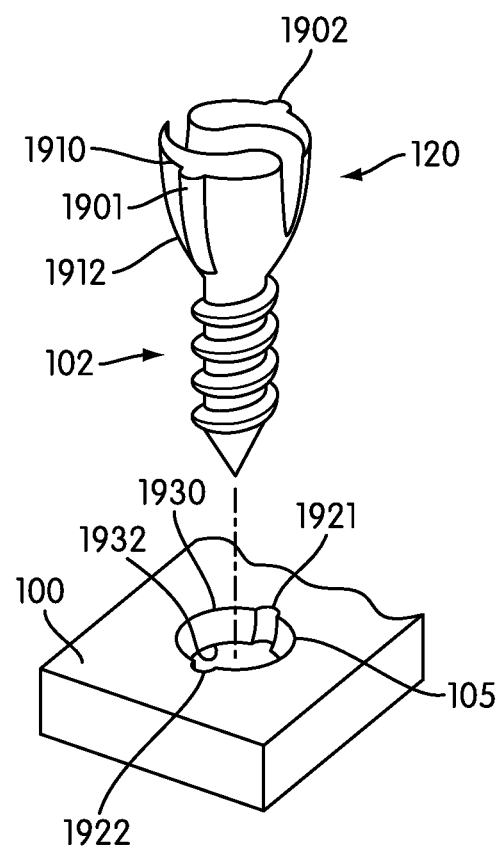
FIG. 20 is an isometric view of a preferred embodiment of a securing member with rib shaped locking protrusions and an implant with channels for receiving the locking protrusions.

FIGS. 18-20 illustrate alternative embodiments of securing member 102, including locking protrusions disposed on different portions of securing member 102. Referring to FIG. 18, a cross sectional view of securing member 102 and implant 100, drive receiving portion 120 may include upper portion 1710, lower portion 1712 and intermediate portion 1714 disposed between upper portion 1710 and lower portion 1712. Preferably, drive receiving portion 120 further includes first locking protrusion 1701 and second locking protrusion 1702 that are disposed on intermediate portion 1714.

Preferably, first securing hole 105 includes provisions for receiving first locking protrusion 1701 and second locking protrusion 1702. In this embodiment, first securing hole 105 may include proximal portion 1720, distal portion 1722 and intermediate portion 1724 that is disposed between proximal portion 1720 and distal portion 1722. In some embodiments, first securing hole 105 can include channels that extend from proximal portion 1720 to distal portion 1722 in order to receive first locking protrusion 1701 and second locking protrusion 1702. In the current embodiment, first securing hole 105 includes first locking recess 1731 and second locking recess 1732 that are disposed within intermediate portion 1724 of first securing hole 105. With this preferred arrangement, first locking recess 1731 and second locking recess 1732 may be configured to engage either first locking protrusion 1701 or second locking protrusion 1702 to help prevent the unfastening of securing member 102. This engagement may be similar to the engagement of locking protrusions and locking recesses in the previous embodiment.

Referring to FIG. 19, in another embodiment, locking protrusions may be associated with lower portion 1712 of drive receiving portion 120. In particular, drive receiving portion 120 may include first locking protrusion 1801 and second locking protrusion 1802 that are disposed on lower portion 1712. Likewise, securing hole 105 preferably includes provisions for locking protrusions within distal portion 1722. In this embodiment, securing hole 105 includes first locking recess 1831 and second locking recess 1832 disposed in distal portion 1722. In some cases, first locking recess 1831 and second locking recess 1832 may be open to lower surface 1810 of implant 100. With this arrangement, first locking recess 1831 and second locking recess 1832 may be configured to engage either first locking protrusion 1801 or second locking protrusion 1802 to help prevent the unfastening of securing member 102. This engagement may be similar to the engagement of locking protrusions and locking recesses in the previous embodiment.

Referring to FIG. 20, a securing member could include a rib-like locking protrusion. In some embodiments, securing member 102 may include first locking protrusion 1901 and second locking protrusion 1902. Generally, first locking protrusion 1901 may have an elongated shape. In a preferred embodiment, first locking protrusion 1901 may have a rib-like shape. In particular, first locking protrusion 1901 may extend from upper portion 1910 of drive receiving portion 120 to lower portion 1912 of drive receiving portion. Preferably, second locking protrusion 1902 has a similar shape and orientation to first locking protrusion 1901.

Securing hole 105 may include provisions to receive first locking protrusion 1901 and second locking protrusion 1902. In some embodiments, securing hole 105 may include first channel 1921 and second channel 1922. Preferably, first channel 1921 and second channel 1922 each extend from proximal portion 1930 to distal portion 1932 of implant securing hole 105. With this arrangement, first channel 1921 and second channel 1922 can be configured to receive either first locking protrusion 1901 or second locking protrusion 1902 to help prevent an unfastening of securing member 102.

The embodiments discussed here for the location and type of locking protrusions and associated locking recesses or channels are intended to be exemplary. It should be understood that in other embodiments any combination of protrusions can be associated with any portions of a drive receiving portion of a securing member. Furthermore, any complementary combination of recesses and/or channels could be associated with any portion of a securing hole of an implant. In some cases, for example, round shaped locking protrusions could be used in combination with rib shaped locking protrusions.

Figure 21:
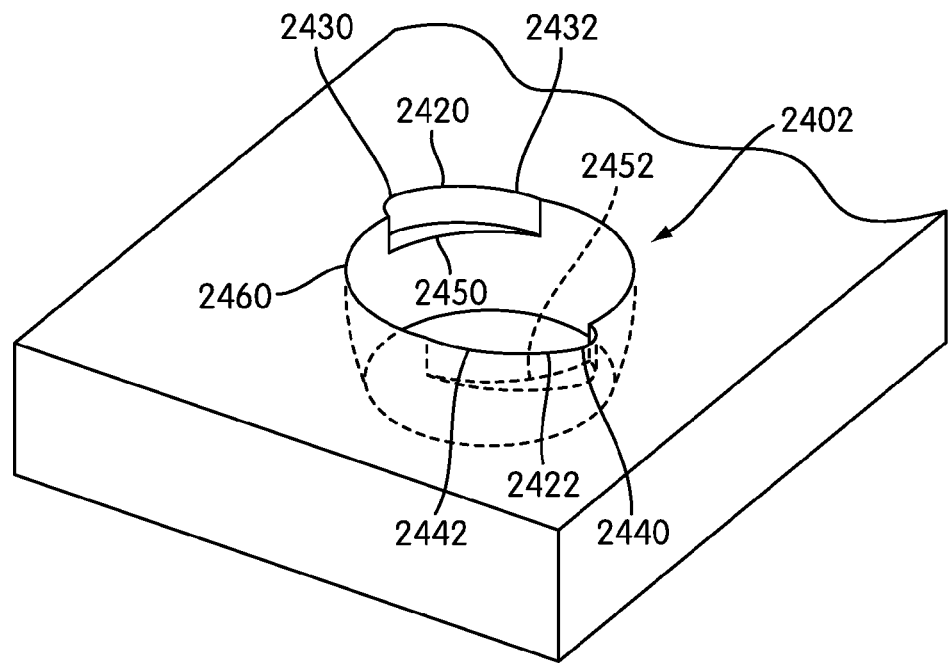
FIG. 21 is a close up view of a preferred embodiment of a securing hole with tapered recesses.
Figure 22:
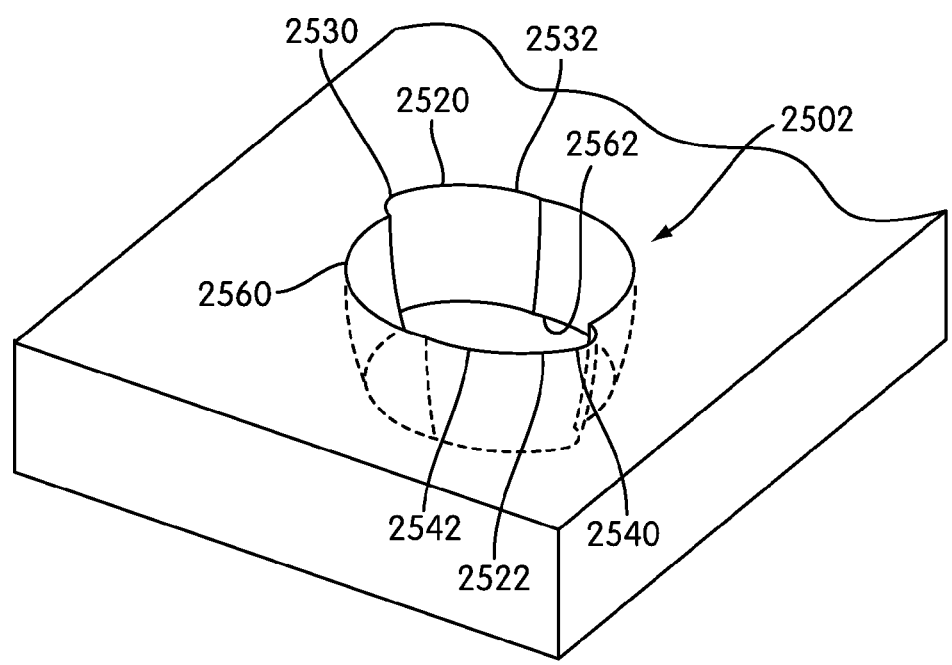
FIG. 22 is a close up view of a preferred embodiment of a securing hole with tapered channels.

Referring to FIGS. 21 and 22, locking recesses or channels could be tapered to allow for easy rotation in the fastening direction. FIG. 21 illustrates an enlarged view of an alternative embodiment of a securing hole of an implant. In this embodiment, securing hole 2402 is configured with tapered recesses that are configured to engage one or more locking protrusions. In some embodiments, securing hole 2402 may include first tapered recess 2420 and second tapered recess 2422. First tapered recess 2420 and second tapered recess 2422 may be similar to the types of recesses discussed in previous embodiments. In particular, first tapered recess 2420 and second tapered recess 2422 may be associated with first lower recess surface 2450 and second lower recess surface 2452, respectively.

Preferably, first tapered recess 2420 includes first widened portion 2430 and first narrow portion 2432. In some cases, first widened portion 2430 may be separated from first narrow portion 2432 by a circumferential distance that is approximately one quarter of the circumference of securing hole 2402. In other embodiments, the separation between first widened portion 2430 and first narrow portion 2432 could vary between zero and one half of the circumference of securing hole 2402.

In some embodiments, securing hole 2402 may also include second tapered recess 2422. Preferably, second tapered recess 2422 includes second widened portion 2440 and second narrow portion 2442. In some cases, second widened portion 2440 may be separated from second narrow portion 2442 by a circumferential distance that is approximately one quarter of the circumference of securing hole 2402. In other embodiments, the separation between second widened portion 2440 and second narrow portion 2442 could vary between zero and one half of the circumference of securing hole 2402.

With this arrangement, as a securing member is rotated with respect to securing hole 2402, one or more locking protrusions may engage with first tapered recess 2420 and second tapered recess 2422. As a securing member is tightened within securing hole 2402, locking protrusions of the securing member can be guided from first widened portion 2430 to first narrow portion 2432. This arrangement may help prevent the locking protrusions from prematurely locking within first tapered recess 2420 as the securing member rotates in the fastening direction. However, once the securing member has been fully fastened in place, first widened portion 2430 may prevent a locking protrusion from slipping out of first tapered recess 2420 in an unfastening direction.

Preferably, locking protrusions can be guided through second tapered recess 2422 in a similar manner as that described for first tapered recess 2420. This arrangement may help the locking protrusions from prematurely locking in second tapered recess 2422 as the securing member is rotated in a fastening direction. Furthermore, second widened portion 2440 preferably helps prevent a locking protrusion from escaping from second tapered recess 2422 when the drive receiving portion is rotated in an unfastening direction.

FIG. 22 illustrates an enlarged view of an alternative embodiment of a securing hole of an implant. In this embodiment, securing hole 2502 is configured with tapered channels that are configured to engage one or more rib-shaped locking protrusions. In some embodiments, securing hole 2502 may include first tapered channel 2520 and second tapered channel 2522. In particular, first tapered channel 2520 and second tapered channel 2522 are preferably similar to the channels discussed in a previous embodiment and illustrated in FIGS. 20 and 21. For example, first tapered channel 2520 and second tapered channel 2522 are open at both upper periphery 2560 and lower periphery 2562 of securing hole 2502.

Preferably, first tapered channel 2520 includes first widened portion 2530 and first narrow portion 2532. In some cases, first widened portion 2530 may be separated from first narrow portion 2532 by a circumferential distance that is approximately one quarter of the circumference of securing hole 2502. In other embodiments, the separation between first widened portion 2530 and first narrow portion 2532 could vary between zero and one half of the circumference of securing hole 2502.

In some embodiments, securing hole 2502 may also include second tapered channel 2522. Preferably, second tapered channel 2522 includes second widened portion 2540 and second narrow portion 2542. In some cases, second widened portion 2540 may be separated from second narrow portion 2542 by a circumferential distance that is approximately one quarter of the circumference of securing hole 2502. In other embodiments, the separation between second widened portion 2540 and second narrow portion 2542 could vary between zero and one half of the circumference of securing hole 2502.

With this arrangement, as a securing member is rotated with respect to securing hole 2502, one or more rib shaped locking protrusions may engage with first tapered channel 2520 and second tapered channel 2522. As a securing member is tightened within securing hole 2502, locking protrusions of the securing member can be guided from first widened portion 2530 to first narrow portion 2532. This arrangement may help prevent the locking protrusions from prematurely locking within first tapered recess 2520 as the securing member rotates in the fastening direction. However, once the securing member has been fully fastened in place, first widened portion 2530 may help prevent a locking protrusion from slipping out of first tapered channel 2520 in an unfastening direction.

Preferably, a second locking protrusion can be guided through second tapered channel 2522 in a similar manner as that described for first tapered channel 2520. This arrangement may help the locking protrusions from prematurely locking in second tapered recess 2522 as the securing member is rotated in a fastening direction. Furthermore, second widened portion 2540 preferably helps prevent a locking protrusion from escaping from second tapered channel 2522 when the drive receiving portion is rotated in an unfastening direction.

Figure 23:
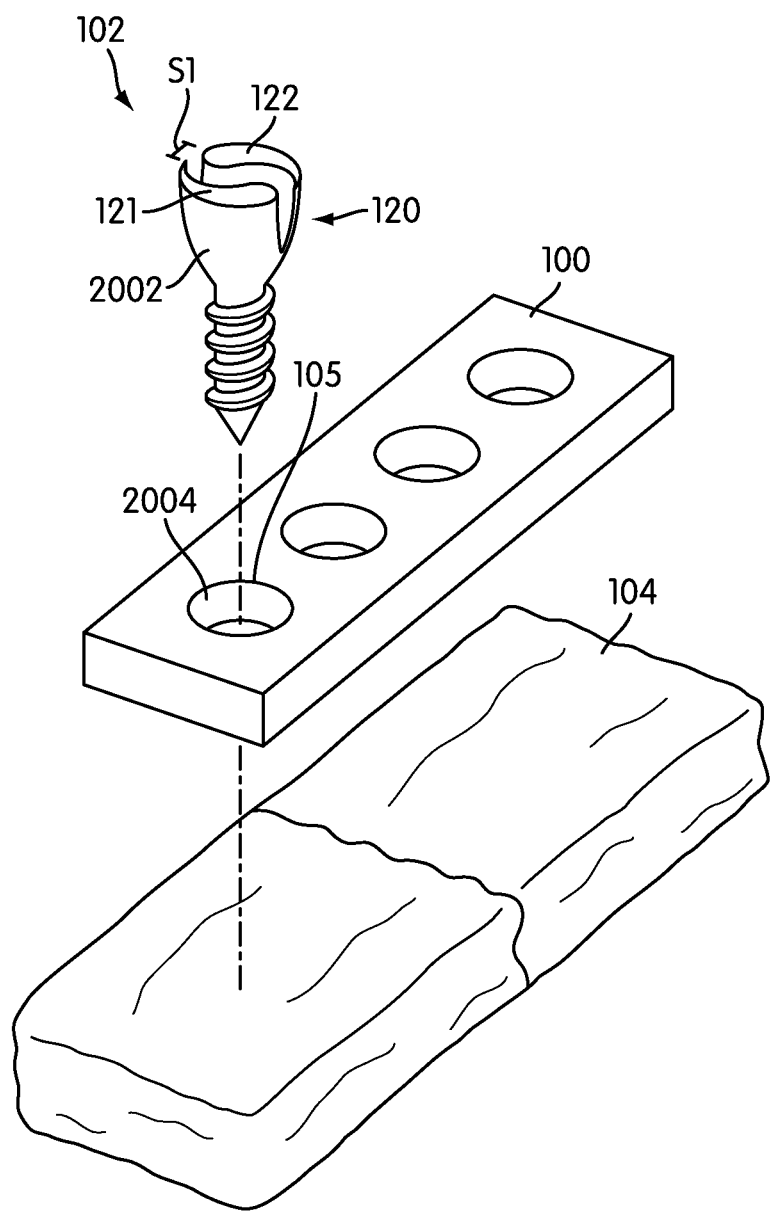
FIG. 23 is an exploded isometric view of a preferred embodiment of a securing member without locking protrusions.
Figure 24:
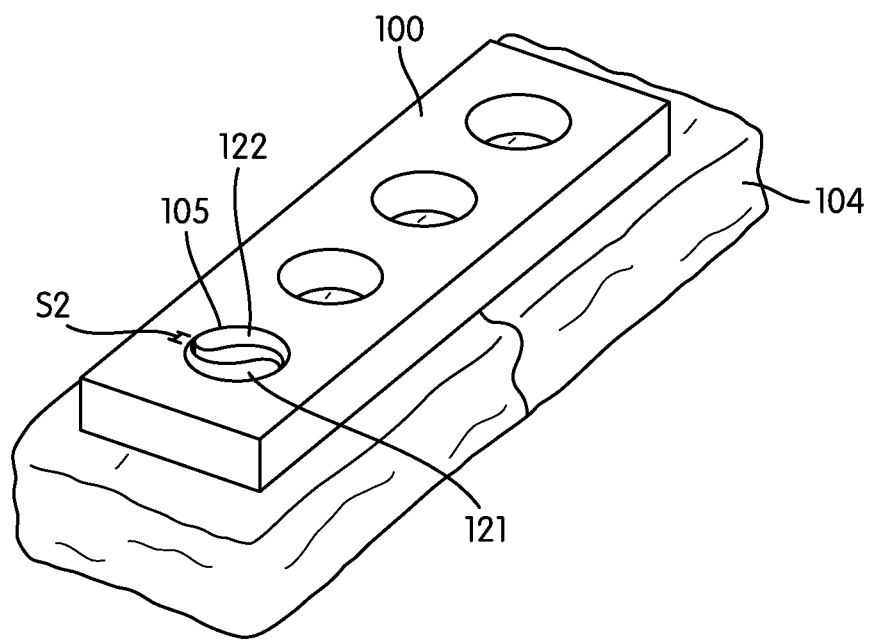
FIG. 24 is an assembled isometric view of a preferred embodiment of a securing member without locking protrusions.

FIGS. 23 and 24 illustrate another embodiment of a securing member without locking protrusions. Referring to FIG. 23, outer portion 2002 of drive receiving portion 120 may be substantially smooth. Preferably, outer portion 2002 is rounded in order to engage side wall portion 2004 of securing hole 105. Also, side wall portion 2004 is preferably smooth without any channels or recesses. In this embodiment, drive receiving portion 120 may be inserted through securing hole 105 in a similar manner to the method of insertion discussed in the previous embodiments.

As drive receiving portion 120 is inserted, first deflecting portion 121 and second deflecting portion 122 may be squeezed together. In particular, first deflecting potion 121 and second deflecting portion 122 may be separated by an average separation S1 prior to insertion. Once drive receiving portion 120 has been inserted into securing hole 105, first deflecting portion 121 and second deflecting portion 122 may be separated by an average separation S2. Preferably, average separation S2 is smaller than average separation S1. With this arrangement, securing member 102 may be prevented from unfastening under forces between outer portion 2002 of drive receiving portion 120 and side wall portion 2004 of securing hole 105.

In some embodiments, a securing member may be inserted at an angle to secure an implantable prosthesis to bone. Generally, a securing member may be inserted at any feasible angle for various reasons. In some cases, anatomical considerations may require an angled insertion of a securing member. In other cases, the shape, size or type of fracture may require an angled insertion of a securing member. Preferably, a securing member inserted at an angle may also include provisions for locking into place following insertion into an implantable prosthesis.

Figure 9:
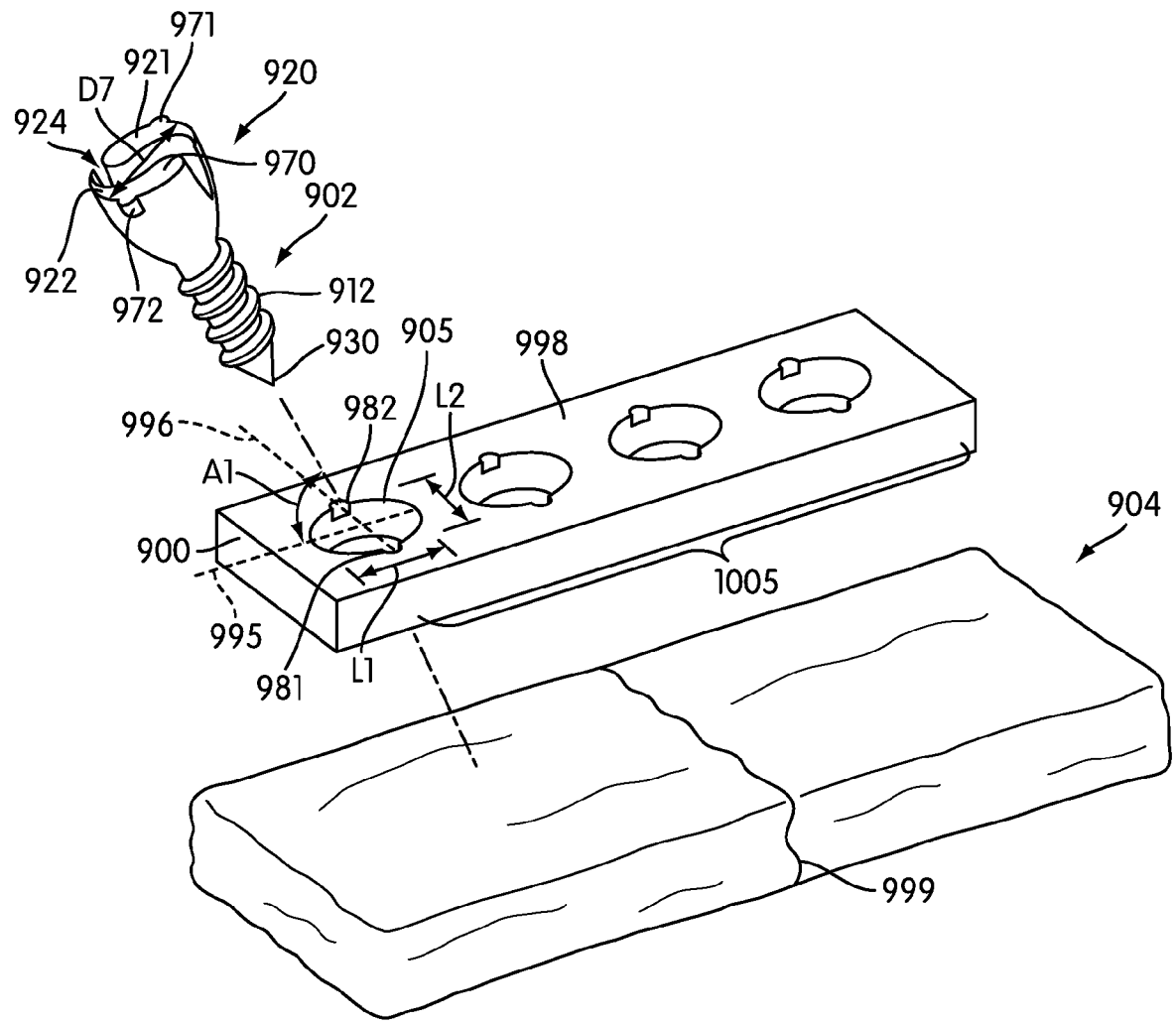
FIG. 9 is an exploded isometric view of an exemplary embodiment of a securing member configured for insertion at an angle through an implant to secure the implant to a bone.

For example, FIGS. 9-11, 25 and 26 illustrate embodiments that have angled securing members. FIG. 9 is an exploded isometric view of an exemplary embodiment of securing member 902 configured to secure implant 900 to bone 904 for healing fracture 999. In this embodiment, implant 900 includes securing hole set 1005. Generally, securing hole set 1005 may include any number of securing holes. In the current embodiment, securing hole set 1005 includes four securing holes. For purposes of clarity, securing member 902 may be associated with securing hole 905 of securing hole set 1005. In a similar manner, additional securing members may be associated with remaining securing holes within securing hole set 1005.

Securing member 902 may include all the features discussed in other embodiments in this detailed description. In the current embodiment, securing member 902 is configured in a similar manner to securing member 102 in the previous embodiment. In particular, securing member 902 includes securing member tip 930 and threaded portion 912. Additionally, securing member 902 includes drive receiving portion 920. Drive receiving portion 920 further includes first deflecting portion 921, second deflecting portion 922 and central cavity 924. As with the previous embodiments, securing member 902 may be fastened by a fastening tool engaging a drive receiving surface within central cavity 924.

Generally, a securing member may be inserted into an implantable prosthesis at various angles. In some embodiments, a securing member may include features for an angled insertion. In other embodiments, a securing member as well as a securing hole may be configured for an angled insertion. In a preferred embodiment, a securing hole may be configured with a particular shape to allow for an angled insertion of a securing member.

Generally, securing member 902 may be inserted at any feasible angle to fasten implant 900 to bone 904. In this embodiment, securing member 902 may be inserted at angle A1 with respect to first side 998 of implant 900. To accommodate the insertion of securing member 902 at angle A1, securing hole 905 may be configured with an elongated shape. Examples of different elongated shapes include, but are not limited to rectangles, regular polygons, ovals, irregular shapes as well as other shapes. In this preferred embodiment, securing hole 905 may have an oval shape.

In this exemplary embodiment, securing hole 905 may include major axis 995. Securing hole 905 may also include minor axis 996. Preferably, major axis 995 has a first length L1. Likewise, minor axis 996 may have a second length L2. In a preferred embodiment, first length L1 is greater than second length L2.

As seen in FIG. 9, securing member 902 may be angled with respect to major axis 995. In some embodiments, length L1 may be larger than diameter D7 of drive receiving portion 920. With this arrangement, major axis 995 may be large enough to accommodate the securing member 902 at an insertion angle A1. In other embodiments, securing member 902 could be angled with respect to minor axis 996. In still other embodiments, securing member 902 could be angled with respect to an axis between major axis 995 and minor axis 996.

Preferably, securing member 902 includes provisions to prevent unwanted movement following the fastening of securing member 902 at angle A1. In the current embodiment, drive receiving portion 920 includes first deflecting portion 921 and second deflecting portion 922. As with the previous embodiment, first deflecting portion 921 and second deflecting portion 922 may undergo inward radial deflection when drive receiving portion 920 is inserted into securing hole 905. In a preferred embodiment, diameter D7 of drive receiving portion 920 is slightly larger than length L2 of minor axis 996 of securing hole 905. With this preferred arrangement, first deflecting portion 921 and second deflecting portion 922 may undergo inward deflection when drive receiving portion 920 is fastened within securing hole 905.

In a similar manner to the previous embodiment, first deflecting portion 921 and second deflecting portion 922 include first locking protrusion 971 and second locking protrusion 972, respectively, on top surface 970 of drive receiving portion 920. Additionally, securing hole 905 includes recesses configured to engage first locking protrusion 971 and second locking protrusion 972 when securing member 902 is fastened to implant 900. In the current embodiment, securing hole 905 includes first locking recess 981 and second locking recess 982. This arrangement preferably allows first locking recess 981 and second locking recess 982 to engage either first locking protrusion 971 or second locking protrusion 972 after fastening securing member 902 into implant 900 at insertion angle A1.

Figure 10:
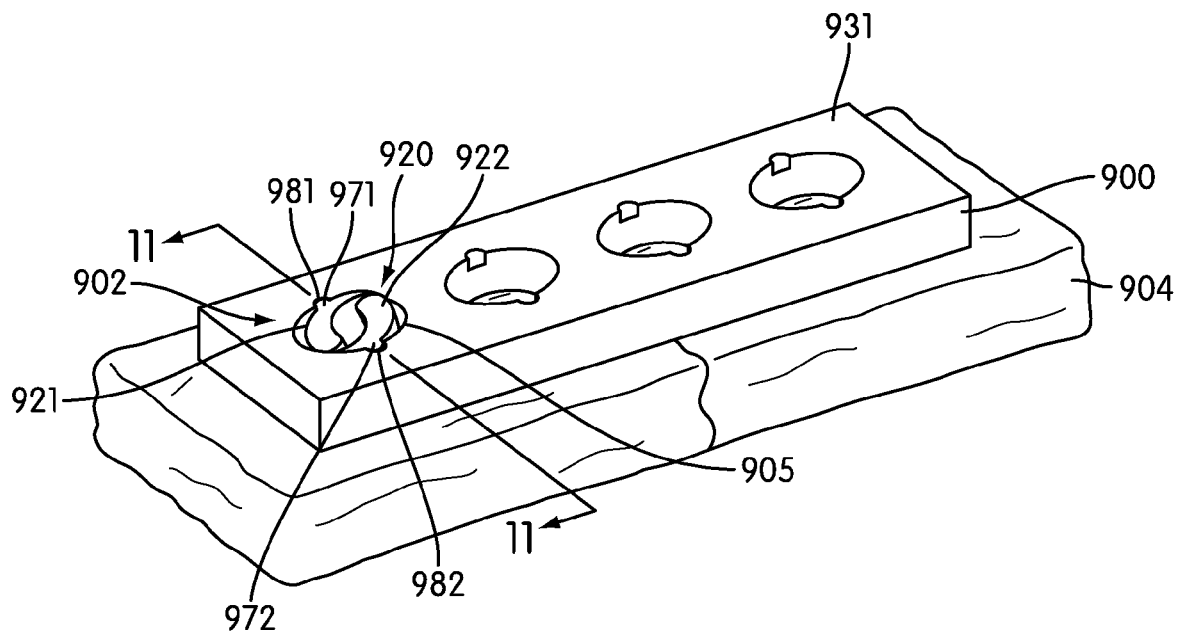
FIG. 10 is an isometric view of an exemplary embodiment of a securing member fastened to an implant at an angle to secure the implant to a bone.
Figure 11:
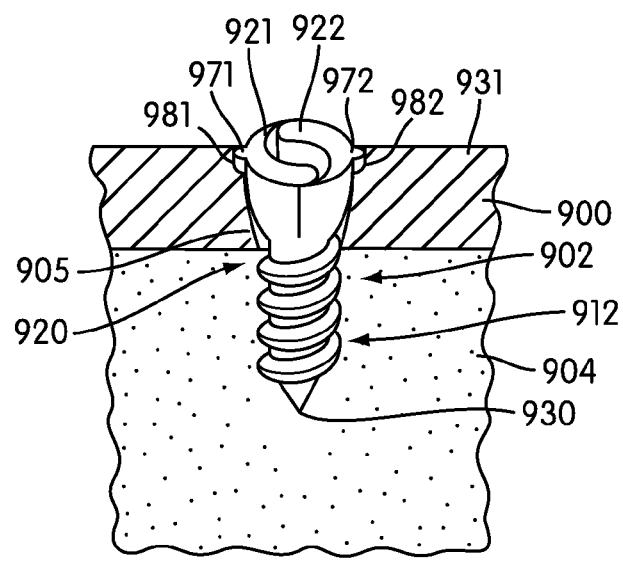
FIG. 11 is a cross sectional view of an exemplary embodiment of a securing member fastened to an implant at an angle to secure the implant to a bone.

FIGS. 10 and 11 illustrate an exemplary embodiment of securing member 902 fully fastened to implant 900 following insertion at angle A1. Typically, securing member 902 may be inserted and fastened in a manner similar to the previous embodiment. With securing member 902 fastened to implant 900, drive receiving portion 920 may be disposed within securing hole 905. In this embodiment, drive receiving portion 920 may not be flush with first side 931 of implant 900 and instead remain at angle A1. However, securing member 902 remains embedded with securing member tip 930 in bone 904 and engaged with threaded portion 912 as seen in FIG. 11. Using this configuration, securing member 902 may fasten implant 900 to bone 904.

Preferably, as securing member 902 is fastened within securing hole 905 at angle A1, first deflecting portion 921 and second deflecting portion 922 deflect radially inward to accommodate the difference in diameters of securing hole 905 and drive receiving portion 920. Additionally, first locking protrusion 971 and second locking protrusion 972 have locked into first locking recess 981 and second locking recess 982, respectively. Alternatively, in other embodiments, first locking protrusion 971 may fit within second locking recess 982 and second locking protrusion 972 may fit into first locking recess 981. Using this configuration, securing member 902 may resist unwanted movement and remain fully fastened within securing hole 905 and bone 902.

In some embodiments, the shape of drive receiving portion 920 could vary. In some cases, drive receiving portion 920 could be rounded to provide a generally smooth and rounded surface following the insertion of securing member 902 at an angle. In particular, one or more deflecting portions could include rounded portions at a proximal end portion of securing member 902.

Figure 25:
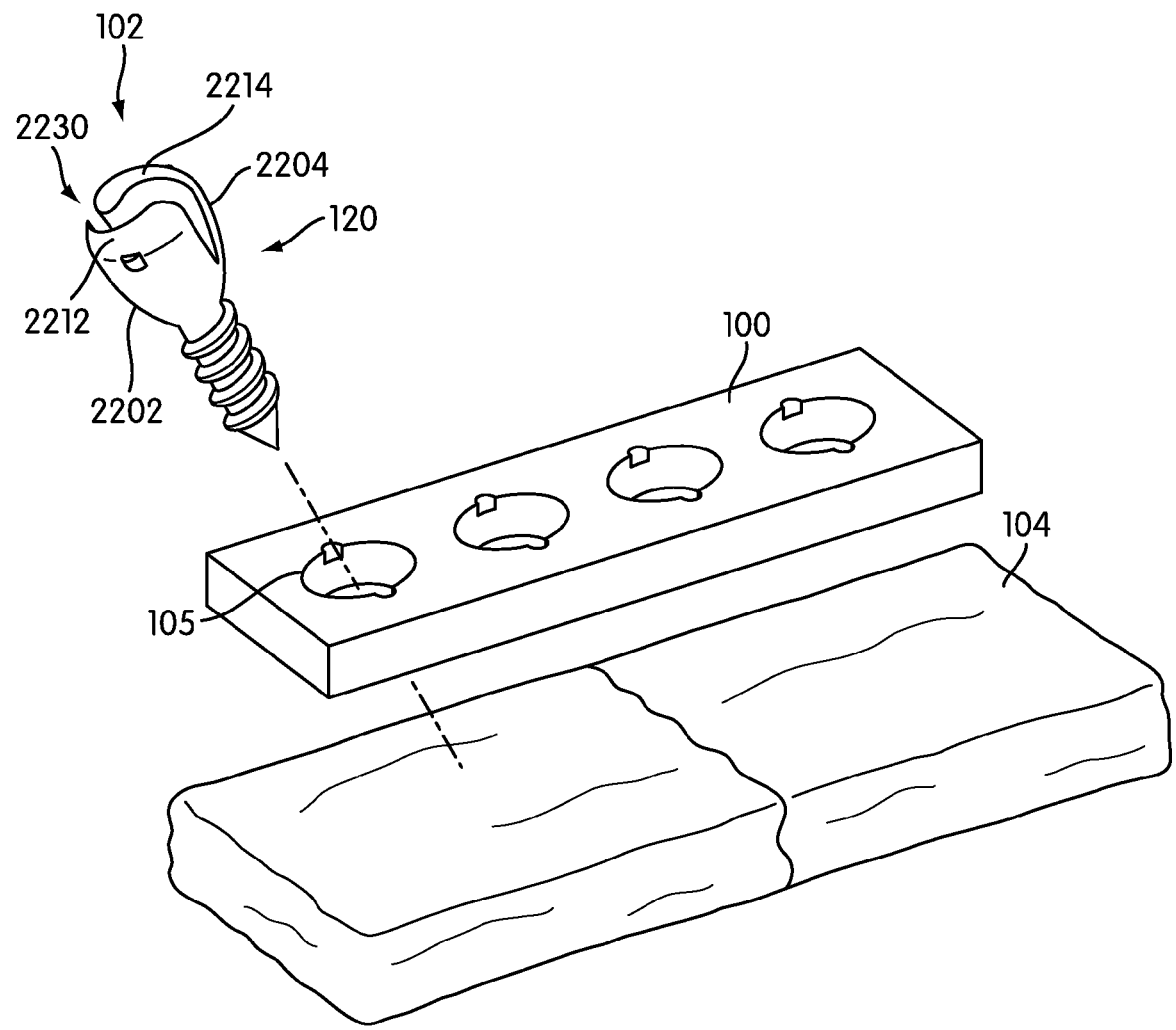
FIG. 25 is an exploded isometric view of a preferred embodiment of a securing member with a rounded proximal portion.
Figure 26:
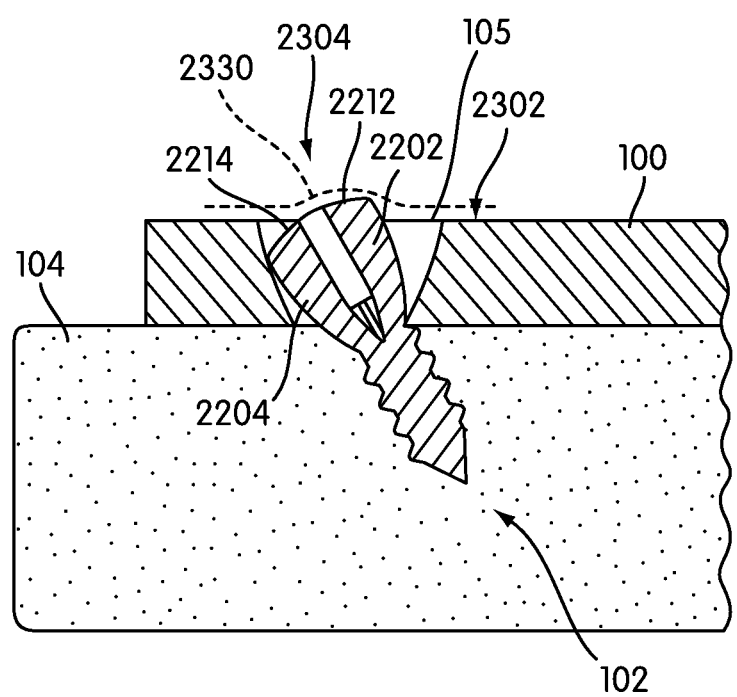
FIG. 26 is a side assembled view of a preferred embodiment of a securing member with a rounded proximal portion.

Referring to FIGS. 25 and 26, drive receiving portion 120 may include first deflecting portion 2202 and second deflecting portion 2204. Preferably, first deflecting portion 2202 includes first rounded portion 2212 at proximal portion 2230 of securing member 102. Likewise, second deflecting portion 2204 may include second rounded portion 2214 at proximal portion 2230. Using rounded deflecting portions can help provide a smooth proximal surface for securing member 102 and prosthesis 100.

As seen in FIG. 26, implant 100 may include a generally flat proximal surface 2302. Additionally, protruding portion 2304 of securing member 102 may be disposed above securing hole 105 adjacent to proximal surface 2302. Since first deflecting portion 2202 and second deflecting portion 2204 are generally rounded at first rounded portion 2212 and second rounded portion 2214, respectively, first protruding portion 2304 may present a generally smooth and rounded surface that is disposed adjacent to proximal surface 2302. In particular, first protruding 2304 and proximal surface 2302 may form a smooth outer surface 2330. This smooth outer surface of implant 100 and securing member 102 can reduce sharp edges that may irritate or otherwise interfere with adjacent tissue.

While the previous embodiments included securing members with two deflecting portions, in other embodiments, a securing member may include any number of deflecting portions. In some cases, changing the number of deflecting portions may change the deflection and/or deformation properties of the securing member. Additionally, various configurations of deflecting portions may allow for adjustment of tensioning forces with a securing hole when a securing member is inserted into an implant.

Figure 12:
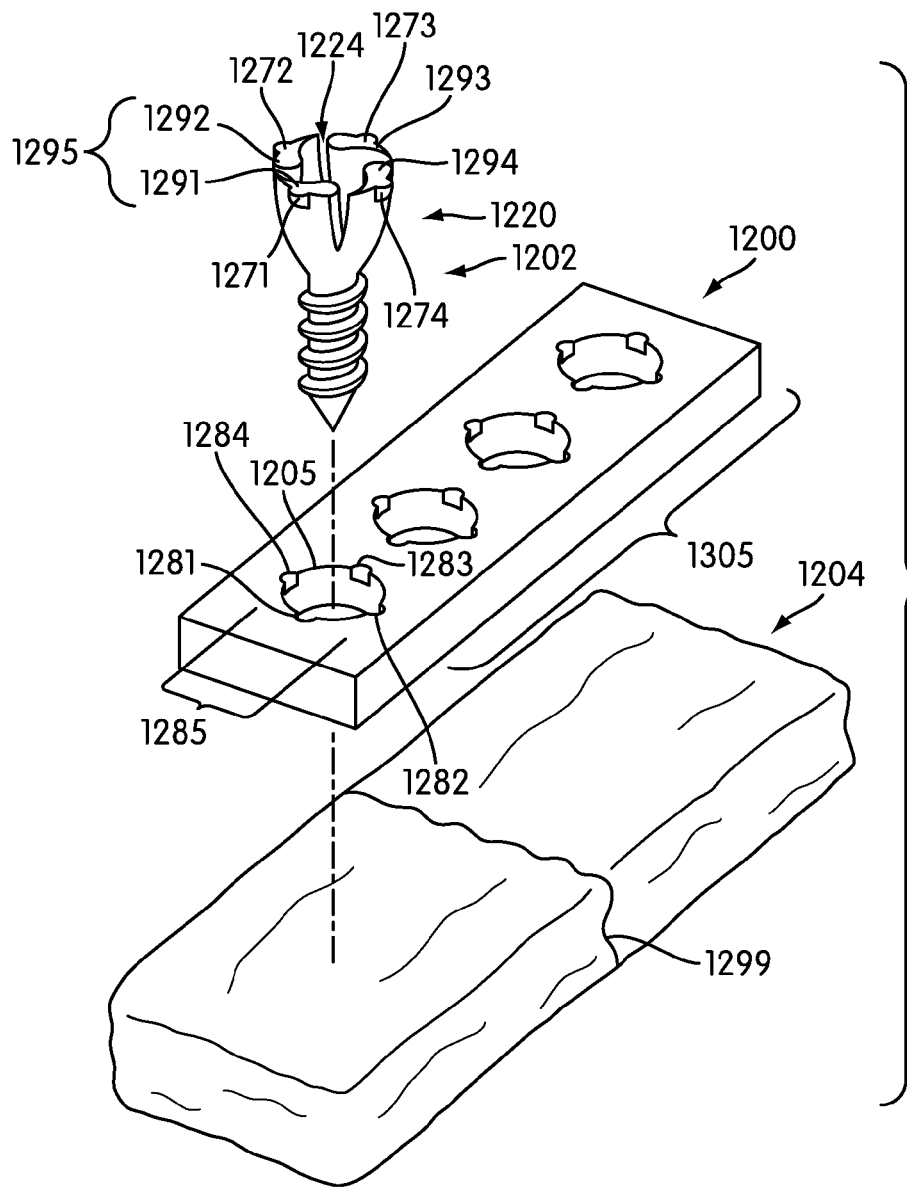
FIG. 12 is an exploded isometric view of an exemplary embodiment of a securing member with four deflecting portions that is configured to secure an implant to a bone.

FIGS. 12-15 illustrate exemplary embodiments of securing members with alternative numbers of deflecting portions. Referring to FIG. 12, securing member 1202 is configured to fasten implant 1200 to bone 1204. In this embodiment, implant 1200 may reinforce fracture 1299 within bone 1204. To fasten to bone 1204, implant 1200 includes securing hole set 1305. Generally, securing hole set 1305 may include any number of securing holes. In the current embodiment, securing hole set 1305 includes four securing holes. In some embodiments, securing holes within securing hole set 1305 may be configured in different manners. For example, a subset of securing hole set 1305 may be configured for an angled securing member insertion. In the current embodiment, the securing holes within securing hole set 1305 are similar. For purposes of clarity, securing member 1202 may be associated with securing hole 1205 of securing hole set 1305. As previously discussed, additional securing members may be associated with the remaining securing holes of securing hole set 1305.

In this embodiment, securing member 1202 includes drive receiving portion 1220. Furthermore, drive receiving portion 1220 includes central cavity 1224. Surrounding central cavity 1224, drive receiving portion 1220 is configured with first deflecting portion 1291, second deflecting portion 1292, third deflecting portion 1293, and fourth deflecting portion 1294 referred to collectively as deflecting portion set 1295. Preferably, adjacent deflecting portions within deflecting portion set 1295 may be separated by a small distance.

Figure 13:
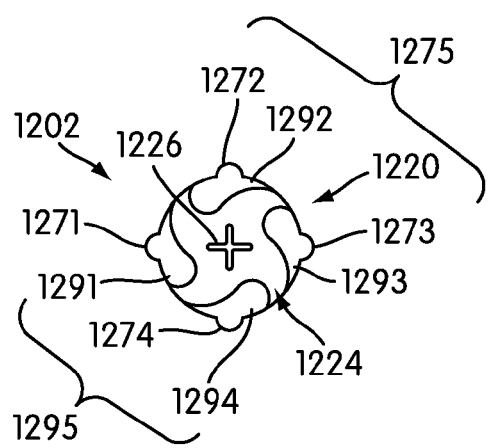
FIG. 13 is a top view of an exemplary embodiment of a securing member with four deflecting portions.

As seen in FIG. 13, drive receiving portion 1220 also includes drive receiving surface 1226 disposed within central cavity 1224. Preferably, drive receiving surface 1226 may engage a fastening tool to fasten securing member 1202 to implant 1200 and bone 1204. As securing member 1202 is fastened, deflecting portion set 1295 may undergo inward deflection as drive receiving portion 1220 is disposed within securing hole 1205.

In this embodiment, first deflecting portion 1291, second deflecting portion 1292, third deflecting portion 1293 and fourth deflecting portion 1294 have a similar shape. In particular, each deflecting portion includes a rounded head with a tapering tail. With this arrangement, if deflecting portion set 1295 is deflected inwardly, the shape of deflecting portion set 1295 may provide a gap at the center of drive receiving portion 1220. This may be helpful by providing a space for a fastening tool so that deflecting portion set 1295 does not impinge on the fastening tool when deflecting portion set 1295 undergoes inward deflection. Additionally, using four generally evenly spaced deflecting portions may help drive receiving portion 1202 maintain a generally circular shape as deflecting portion set 1295 deflects.

Deflecting portion set 1295 may also include locking protrusions in order to secure securing member 1202 in place within securing hole 1205. In particular, first deflecting portion 1291, second deflecting portion 1292, third deflecting portion 1293 and fourth deflecting portion 1294 may include first locking protrusion 1271, second locking protrusion 1272, third locking protrusion 1273 and fourth locking protrusion 1274, respectively. First locking protrusion 1271, second locking protrusion 1272, third locking protrusion 1273 and fourth locking protrusion 1274 may be referred to collectively as locking protrusion set 1275.

In a similar manner, securing hole 1205 includes first locking recess 1281, second locking recess 1282, third recess 1283 and fourth recess 1284 referred to collectively as recess set 1285. Preferably, recesses within recess set 1285 have a complementary shape in order to fit with the locking protrusions within locking protrusion set 1275, but it is understood that it could have a non-complementary shape or any appropriate shape. In addition, locking protrusion set 1275 and recess set 1285 may be spaced evenly so that all locking protrusions within locking protrusion set 1275 may align with recesses within recess set 1285 to fasten securing member 1202 within securing hole 1205. With this arrangement, securing member 1202 may resist unfastening following insertion into implant 1200 and bone 1204.

Alternatively, a securing member with three deflecting portions may also be configured to undergo inward deflection upon insertion in an implant. FIGS. 14-15 illustrate an exemplary embodiment of securing member 1402 configured to attach implant 1400 to bone 1404 in order to reinforce fracture 1499. This embodiment may be similar to the previous embodiment. In particular, implant 1400 includes securing hole set 1505 with four similar securing holes. As previously mentioned, securing hole set 1505 may include any number of securing holes configured in various manners. For illustrative purposes, securing member 1402 may be associated with securing hole 1405 of securing hole set 1505. Securing members similar to securing member 1402 may be fastened within remaining securing holes in securing hole set 1505 in a similar manner.

In a similar manner to the previous embodiment, securing member 1402 includes drive receiving portion 1420 configured with central cavity 1424. In some embodiments, drive receiving portion 1420 may include three deflecting portions. In this embodiment, drive receiving portion 1420 is configured with first deflecting portion 1491, second deflecting portion 1492, and third deflecting portion 1493 referred to collectively as deflecting portion set 1495. In a preferred embodiment, deflecting portion set 1495 may be configured to undergo inward deflection during insertion of securing member 1402.

Adjacent deflecting portions within deflecting portion set 1495 may be separated by a small distance. This spacing allows for inward deflection of deflecting portion set 1495. Furthermore, as deflecting portion set 1495 deflects, this spacing between adjacent deflecting portions may decrease, which further decreases the overall circumference of drive receiving portion 1420. With this arrangement, deflecting portion set 1495 deflects to create a tighter fit within securing hole 1405 as when securing member 1402 is fastened to implant 1400.

Referring to FIG. 15, central cavity 1424 includes drive receiving surface 1426. Drive receiving surface 1426 is configured to engage a fastening tool in order to fasten securing member 1402 to implant 1400 and bone 1404. In some embodiments, as deflecting portion set 1495 undergoes inward deflection, the arrangement of deflecting portion set 1495 may help prevent central cavity 1424 from completely closing. This arrangement may allow a fastening tool to remain engaged to tighten securing member 102 completely in place.

Generally, deflecting portions within deflecting portion set 1495 may have any shape. In this embodiment, deflecting portion set 1495 is shaped and configured in a similar manner to the previous embodiment with a rounded head and a tapering tail. These shapes provide a complementary nesting arrangement for deflecting portion set 1495.

Furthermore, deflecting portion set 1495 also include locking protrusions to secure securing member 1402 in place within securing hole 1405. In particular, first deflecting portion 1491, second deflecting portion 1492, and third deflecting portion 1493 include first locking protrusion 1471, second locking protrusion 1472, and third locking protrusion 1473, respectively. First locking protrusion 1471, second locking protrusion 1472, and third locking protrusion 1473 may be referred to collectively as locking protrusion set 1475. Generally, locking protrusion set 1475 may include any particular shape. In addition, securing hole 1405 preferably includes first locking recess 1481, second locking recess 1482, and third recess 1483 referred to collectively as recess set 1485. Preferably, recess set 1485 includes shapes complementary to locking protrusion set 1475. Also, locking protrusion set 1245 and recess set 1485 may be spaced evenly so that all locking protrusions within locking protrusion set 1475 may align with recesses within recess set 1485 to secure securing member 1402 within securing hole 1405. With this arrangement, securing member 1402 may be securely fastened within securing hole 1405 and resist twisting that may result in unfastening from implant 1400 and bone 1404.

Generally, deflecting portions may be formed in any particular shape that allows deflection in a radially inward direction when a securing member is fastened. In previous embodiments, deflecting portions have included rounded heads with tapered tails. In some embodiments, deflecting portions may be rounded at both ends. In other embodiments, deflecting portions may be configured in a slotted design without rounded ends. This can be accomplished, in some embodiments, by cutting across a top surface of a drive receiving portion.

FIGS. 16-17 illustrate an exemplary embodiment of securing member 1602 configured with a slotted design. In this embodiment, securing member 1602 may fasten implant 1600 to bone 1604 to reinforce fracture 1699. To fasten to bone 1604, implant 1600 includes securing hole set 1705 comprising four securing holes. For purposes of clarity, securing member 1602 may be associated with securing hole 1605 of securing hole set 1705. Additional securing members may be associated with the remaining securing holes of securing hole set 1705.

As in the previous embodiments, drive receiving portion 1620 of securing member 1602 includes central cavity 1624. In some embodiments, drive receiving portion 1620 may be associated with four deflecting portions. In this embodiment, drive receiving portion 1620 is configured with first deflecting portion 1691, second deflecting portion 1692, third deflecting portion 1693 and fourth deflecting portion 1694 referred to collectively as deflecting portion set 1695.

Central cavity 1624 also includes drive receiving surface 1626 as seen in FIG. 17. Drive receiving surface 1626 may engage a fastening tool to fasten securing member 1602 to implant 1600 and bone 1604. As a fastening tool fastens securing member 1602, deflecting portion set 1695 preferably undergoes inward deflection when drive receiving portion 1620 comes into contact with securing hole 1605.

In this exemplary embodiment, drive receiving portion 1620 has a slotted design. This slotted design includes four regularly spaced slots. In particular, drive receiving portion 1620 includes first slot 1661 that is disposed between first deflecting portion 1691 and second drive receiving portion 1692. Additionally, drive receiving portion 1620 includes second slot 1662 that is disposed between second deflecting portion 1692 and third deflecting portion 1693. Drive receiving portion 1620 also includes third slot 1663 that is disposed between third deflecting portion 1693 and fourth deflecting portion 1694. Finally, drive receiving portion 1620 includes fourth slot 1664 that is disposed between fourth deflecting portion 1694 and first deflecting portion 1691. Generally, first slot 1661, second slot 1662, third slot 1663 and fourth slot 1664 provide regular spacing between adjacent deflecting portions of deflecting portion set 1695.

In some embodiments, this slotted design may provide for even spacing between the edges of deflecting portions of deflecting portion set 1695. In particular, first deflecting portion 1691 and second deflecting portion 1692 may be associated with first edge 1668 and second edge 1667, respectively, that are separated by first slot 1661. In some embodiments, first edge 1668 and second edge 1667 may be generally straight due to the shape of first slot 1661. These straightened edges may provide for a smooth engagement between first deflecting portion 1691 and second deflecting portion 1692 during inward deflection. Therefore, as first deflecting portion 1691 and second deflecting portion 1692 engage during inward deflection, circumferential forces between first deflecting portion 1691 and second deflecting portion 1692 may be evenly distributed. Preferably, each of the remaining deflecting portions are associated with similar straightened edges configured to fit together smoothly following inward deflection.

Generally, deflecting portions associated with deflecting portion set 1695 may have any shape. Examples of various shapes for the deflecting portions have been discussed in previous embodiments, including complementary nesting shapes and segmented annulus shapes. In other embodiments, deflecting portions could have other shapes including, but not limited to, circular shapes, rectangular shapes, triangular shapes, regular polygonal shapes, irregular shapes as well as any other shapes.

In this current embodiment, deflecting portions comprising deflecting portion set 1695 may present a partial annulus shape at the top of drive receiving portion 1620, as seen in FIG. 17. In other words, first deflecting portion 1691, second deflecting portion 1692, third deflecting portion 1693 and fourth deflecting portion 1694 may each present a portion of an annulus that is segmented by first slot 1661, second slot 1662, third slot 1663 and fourth slot 1664.

Preferably, deflecting portion set 1695 may also include locking protrusions in order to lock securing member 1602 in place following insertion. In this embodiment, first deflecting portion 1691, second deflecting portion 1692, third deflecting portion 1693 and fourth deflecting portion 1694 include first locking protrusion 1671, second locking protrusion 1672, third locking protrusion 1673 and fourth locking protrusion 1674, respectively. First locking protrusion 1671, second locking protrusion 1672, third locking protrusion 1673 and fourth locking protrusion 1674 may be referred to collectively as locking protrusion set 1675. Generally, locking protrusion set 1675 may include any particular shape that allows locking protrusion set 1675 to lock into corresponding recesses within securing hole 1605. In particular, securing hole 1605 includes first locking recess 1681, second locking recess 1682, third recess 1683 and fourth recess 1684 referred to collectively as recess set 1685. Preferably, recess set 1685 is configured with spacing and shapes complementary to locking protrusion set 1675. With this preferred arrangement, securing member 1602 may be securely fastened within securing hole 1605 by the inward deflection of deflecting portion set 1695 and the alignment of locking protrusion set 1675 and recess set 1684. This can provide a resistance to twisting that may unfasten securing member 1602 from implant 1600 and bone 1604.

Generally, a drive receiving portion of a securing member can be configured in various shapes. In particular, the drive receiving portion may be configured with any type of taper. In some cases, the drive receiving portion may have a conical taper. In other cases, the drive receiving portion may have a spherical taper. In still other cases, the drive receiving portion may have a U-shaped taper. Additionally, a securing hole can be configured with a shape that substantially matches the drive receiving member. With this arrangement, a securing hole can be shaped to help control the fastening of the securing member.

Figure 27:
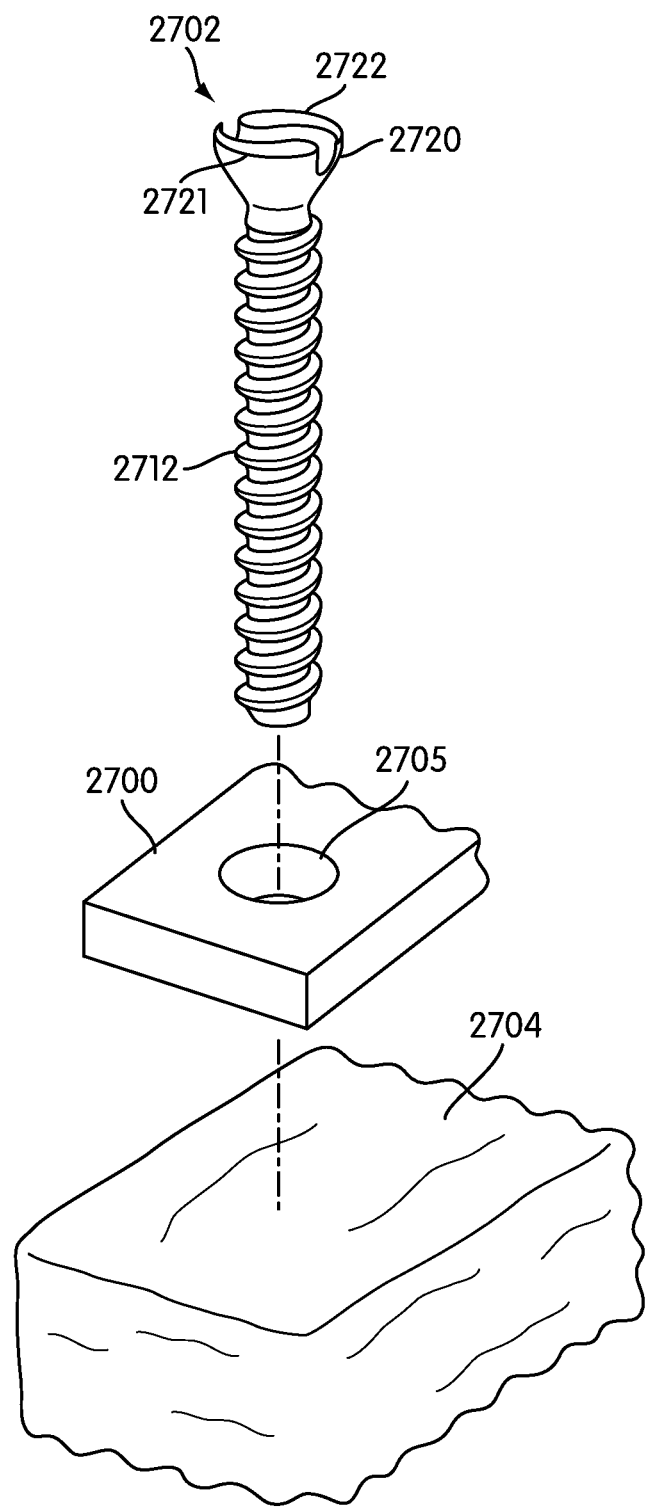
FIG. 27 is an isometric view of a preferred embodiment of a securing member with a drive receiving portion having a conical taper.
Figure 28:
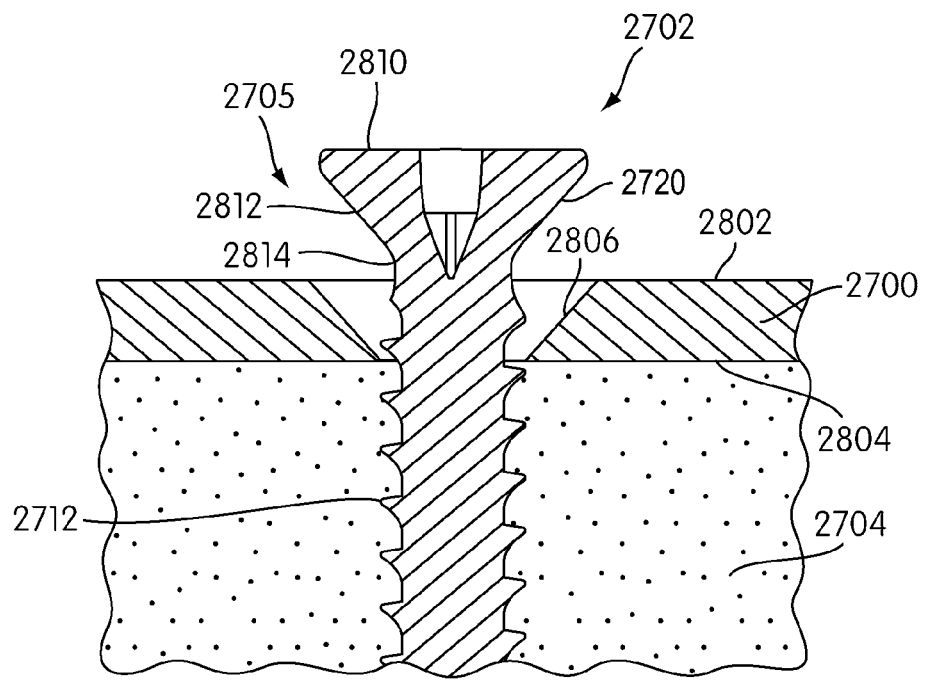
FIG. 28 is a side cross sectional view of a preferred embodiment of a securing member with a drive receiving portion having a conical taper.

FIGS. 27-28 illustrate a preferred embodiment of securing member 2702. In this embodiment, securing member 2702 can be associated with securing hole 2705 to fasten implant 2700 to bone 2704. In particular, securing member 2702 includes drive receiving portion 2720 and threaded portion 2712 to fasten to implant 2700 and bone 2704. Furthermore, securing member 2702 also includes first deflecting portion 2721 and second deflecting portion 2722 to maintain a tight connection between securing member 2702 and implant 2700. In addition, it should be understood that securing member 2702 can also include any combination of features discussed with other embodiments in this detailed description. For example, in some embodiments, securing member 2702 may be provided with locking protrusions that are configured to engage locking recesses disposed in securing hole 2705.

In this preferred embodiment, drive receiving portion 2720 is configured with a conical shape as illustrated in cross section in FIG. 28. Specifically, upper surface 2810 is substantially flat with outer wall 2812 tapering as drive receiving portion 2720 joins threaded portion 2712 at bottom surface 2814 of drive receiving portion 2720.

Preferably, securing hole 2705 is configured to receive securing member 2702 in a manner that assists in preventing drive receiving portion 2720 from entering bone 2704. Typically, securing member 2702 may be fastened into bone 2704 so that upper surface 2810 is substantially flush with first side 2802 of implant 2700 while bottom surface 2814 of drive receiving portion 2720 is disposed proximate to second side 2804 of implant 2700. In order to receive securing member 2702, securing hole 2705 is configured with sloping inner wall 2806 that corresponds to tapered outer wall 2812 of securing member 2702. Using this arrangement, securing member 2702 can be fastened within securing hole 2705 while preventing drive receiving portion 2720 from advancing past second side 2804 of securing hole 2705.

Figure 29:
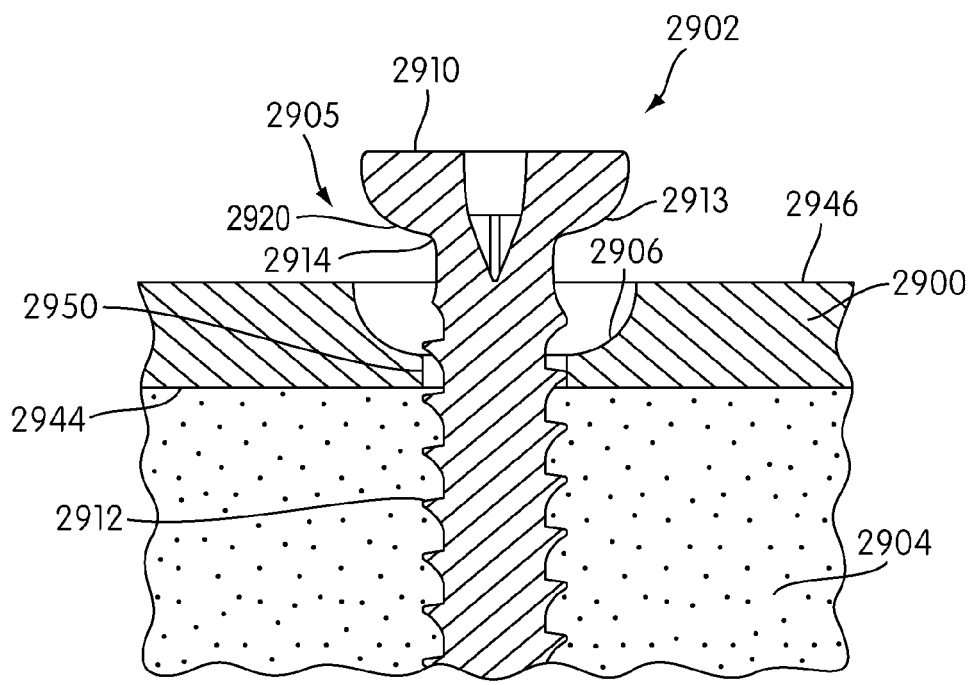
FIG. 29 is a side cross sectional view of a preferred embodiment of a securing member with a drive receiving portion having a spherical taper.

In other embodiments, a drive receiving portion may comprise other shapes that also prevent the drive receiving portion from extending past an implant and into a bone. FIG. 29 is a cross sectional view of an alternative embodiment of securing member 2902. In this embodiment, securing member 2902 includes drive receiving portion 2920 configured with a generally spherical taper. In a similar manner to the other embodiments in this detailed description, securing member 2902 also includes threaded portion 2912.

In this embodiment, drive receiving portion 2920 comprises upper surface 2910, outer wall 2913, and bottom surface 2914 disposed proximate to threaded portion 2912. Furthermore, upper surface 2910 is substantially flat. Also, outer wall 2913 configured with a partial spherical shape that tapers to bottom surface 2914. With this arrangement, the circumference of outer wall 2913 expands from bottom surface 2914 to upper surface 2910.

For purposes of clarity, additional portions of drive receiving portion 2920 are not discussed, but it should be understood that drive receiving portion 2920 can include features discussed with other embodiments in this detailed description. For example, drive receiving portion 2920 could include locking protrusions or rib shaped locking protrusions disposed on any number of deflecting portions.

In this embodiment, securing member 2902 is fastened into securing hole 2905 of implant 2900 to secure implant 2900 to bone 2904. Preferably, securing hole 2905 is configured to correspond with drive receiving portion 2920 of securing member 2902. In particular, inner wall 2906 of securing hole 2905 can be configured with a concave shape. This preferred configuration corresponds with the spherical taper of outer wall 2913 of drive receiving portion 2920. With this arrangement, securing hole 2905 can receive drive receiving portion 2920 when securing member 2902 is fastened to implant 2900.

In some cases, inner wall 2906 may also be configured with a vertical portion 2950 disposed near second side 2944 of implant 2900 that prevents drive receiving portion 2920 from fastening further within securing hole 2905. In other words, inner wall 2906 can include a vertical portion with a width that admits threaded portion 2912 but which does not admit drive receiving portion 2920. This arrangement may prevent over-fastening of drive receiving portion 2920.

Generally, a vertical portion of inner wall 2906 can be configured with any height to allow any portion of drive receiving portion 2920 to be received within securing hole 2905. In this embodiment, inner wall 2906 includes vertical portion 2950. Preferably, vertical portion 2950 is configured with a height that allows the entirety of drive receiving portion 2920 to be secured within securing hole 2905. With this arrangement, upper surface 2910 can be substantially flush with first side 2946 of implant 2900, while inner wall 2906 and vertical portion 2950 block drive receiving portion 2920 from passing through securing hole 2905.

The embodiments included in this detailed description are exemplary. Each of the features discussed here could be used in combination with other features, or could be used independently. In other words, each of the features discussed in this detailed description is optional.

Figure 30:
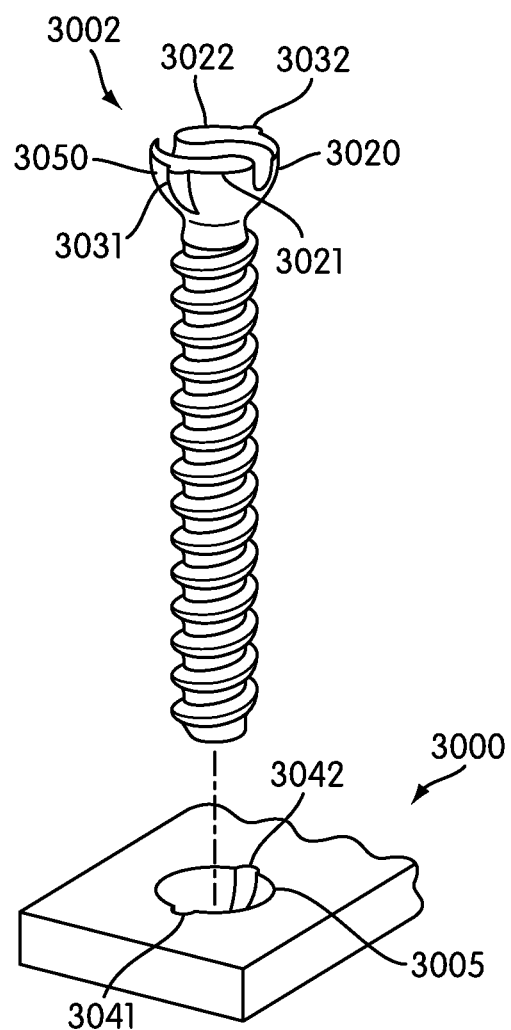
FIG. 30 is an isometric view of a preferred embodiment of a securing member with locking protrusions fastening to an implant configured with channels.

FIG. 30 is an isometric view of an exemplary embodiment of a securing member and securing hole combining features discussed in previous embodiments. In this embodiment, drive receiving portion 3020 of securing member 3002 includes first deflecting portion 3021 and second deflecting portion 3022. Furthermore, first deflecting portion 3021 and second deflecting portion 3022 are configured with first locking protrusion 3031 and second locking protrusion 3032, respectively.

As previously mentioned, first locking protrusion 3031 and second locking protrusion 3032 may be disposed in any location on first deflecting portion 3021 and second deflecting portion 3022, respectively. In this embodiment, first locking protrusion 3031 and second locking protrusion 3032 are disposed on outer walls 3050 of securing member 3002. Additionally, first locking protrusion 3031 and second locking protrusion 3032 are configured with a similar round shape.

In some previous embodiments, a securing member with locking protrusions may be associated with a securing hole configured with locking recesses. However, it is also possible that a securing member with locking protrusions can be associated with a securing hole with other provisions to receive locking protrusions. For example, a securing member with locking protrusions may be associated with a securing hole configured with channels.

In this embodiment, securing member 3002 is associated with securing hole 3005 of implant 3000. Securing hole 3005 is configured with first channel 3041 and second channel 3042. Similar to previous embodiments, first channel 3041 and second channel 3042 preferably extend through the entire height of securing hole 3005. Preferably, first channel 3041 and second channel 3042 are configured with complementary concave shapes that fit the rounded shapes of first locking protrusion 3031 and second locking protrusion 3032. However, first channel 3041 and second channel 3042 generally have a greater height than the height of first locking protrusion 3031 and second locking protrusion 3032. Using this configuration, securing member 3002 may be fastened until desired and first locking protrusion 3031 and second locking protrusion 3032 are engaged in the closest channel, either first channel 3041 or second channel 3042.

In some cases, this arrangement of locking protrusions and channels may allow for greater control in the fastening of securing member 3002 because first channel 3041 and second channel 3042 extend the height of securing hole 3005. In other words, first locking protrusion 3031 and second locking protrusion 3032 can engage any portion of first channel 3041 and second channel 3042 when securing member 3002 is fastened within securing hole 3005.

Generally, a securing member could be configured having any number of deflecting portions. Although securing members with one, two, three and four deflecting portions are discussed in this detailed description, it is obvious that in other embodiments additional deflecting portions could be used. Furthermore, the embodiments discussed in this detailed description included deflecting portions with complementary nesting shapes as well as deflecting portions with segmented annulus shapes, but it is understood that other shapes can be used including non-complementary shapes. Additionally, a securing member may be associated with any number of locking protrusions that may preferably be received by an equal number locking recesses in an implant. In some cases, each deflecting portion of the securing member may include a locking protrusion configured to engage a locking recess on the implant. In other embodiments, some deflecting portions may not include any locking recesses. In still other embodiments, some deflecting portions could include multiple locking protrusions configured to engage multiple locking recesses on the implant. Further, in some cases there could be an unequal number of locking protrusions and locking recesses, such as fewer locking protrusions than locking recesses. In general, any advantageous arrangement and numbers of locking protrusions and locking recesses could be used.

Figure 31:
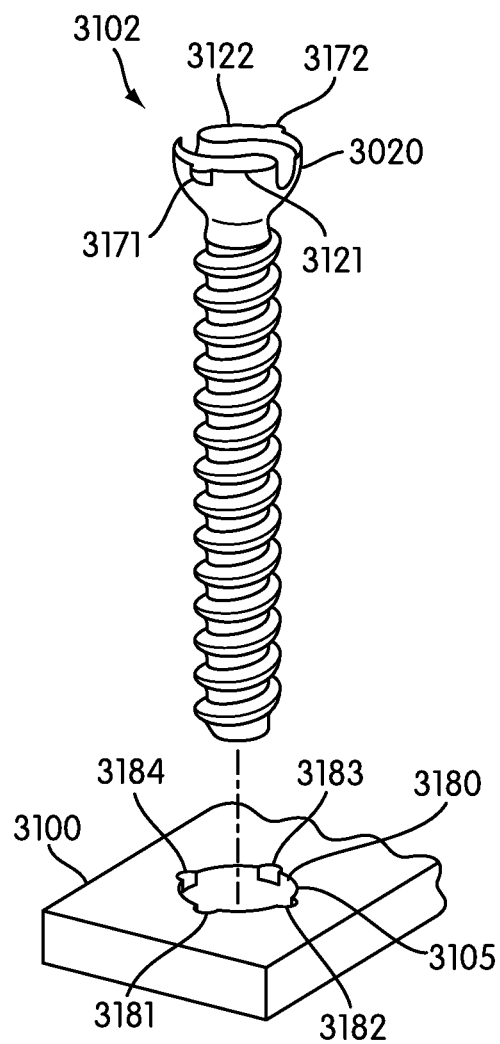
FIG. 31 is an isometric view of a preferred embodiment of a securing member with two locking protrusions fastening to a securing hole of an implant with four locking recesses.

FIG. 31 is an isometric view of an exemplary embodiment of a securing member 3102 configured to fasten implant 3100 to a bone. The bone is not included in this illustration for purposes of clarity. In this exemplary embodiment, securing member 3102 includes first deflecting portion 3121 and second deflecting portion 3122. In addition, first deflecting portion 3121 and second deflecting portion 3122 include first locking protrusion 3171 and second locking protrusion 3172. First locking protrusion 3171 and second locking protrusion 3172 are configured with similar rounded shapes.

It is possible that a securing hole with more than two locking recesses can be associated with securing member 3102. In this embodiment, securing member 3102 is associated with securing hole 3105 of implant strip 3100. Furthermore, securing hole 3105 is configured with first locking recess 3181, second locking recess 3182, third locking recess 3183 and fourth locking recess 3184, collectively referred to as locking recess set 3180. The locking recesses of locking recess set 3180 are disposed in an equally spaced manner on an upper surface of securing hole 3105. Also, the locking recesses of locking recess set 3180 are preferably configured to receive first locking protrusion 3171 and second locking protrusion 3172.

Generally, this configuration of a greater number of locking recesses than locking protrusions allows the fastening of securing member 3102 to implant 3100 to be fine tuned. In other words, this configuration provides additional opportunities for locking protrusions to engage locking recesses when fastening securing member 3102 to implant 3100. For example, in this embodiment, securing member 3102 can be fastened until first locking protrusion 3171 and second locking protrusion 3172 are engaged in the closest locking recess, either first locking recess 3181, second locking recess 3182, third locking recess 3183 or fourth locking recess 3184.

Figure 32:
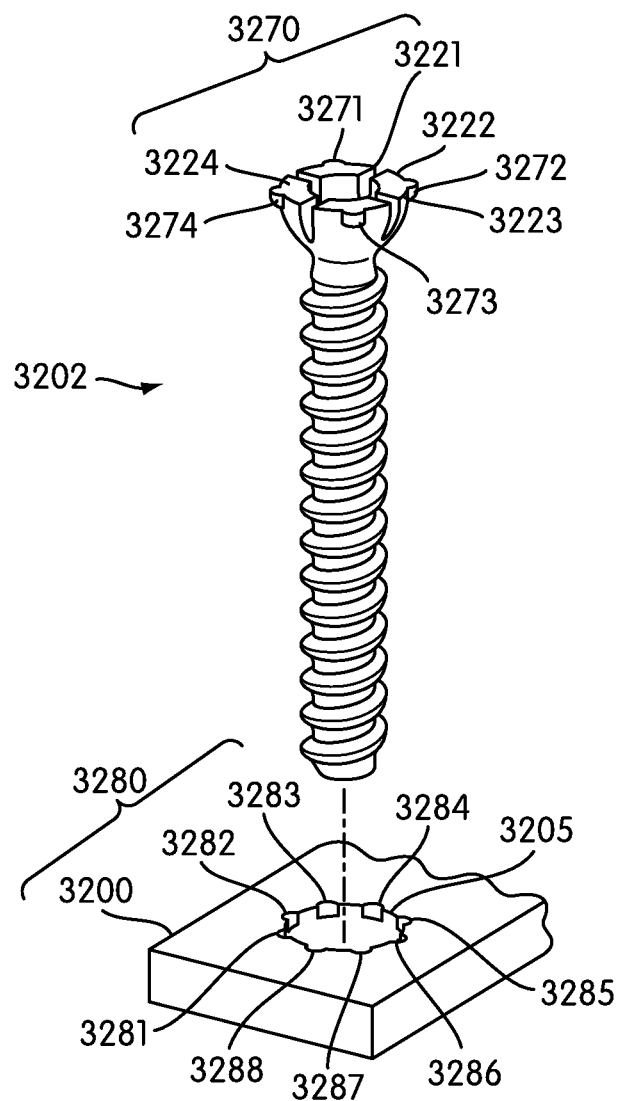
FIG. 32 is an isometric view of a preferred embodiment of a securing member with four locking protrusions fastening to a securing hole of an implant with eight locking recesses.

In some embodiments, the number of locking recesses and locking protrusions can be adjusted to provide greater control in fastening a securing member to an implant and bone. Referring to FIG. 32, securing member 3202 includes locking protrusion set 3270. Preferably, locking protrusion set 3270 includes four locking protrusions. Locking protrusion set 3270 includes first locking protrusion 3271, second locking protrusion 3272, third locking protrusion 3273 and fourth locking protrusion 3274 disposed on first deflecting portion 3221, second deflecting portion 3222, third deflecting portion 3223 and fourth deflecting portion 3224, respectively. Preferably, the locking protrusions of locking protrusion set 3270 comprise similar rounded shapes regularly spaced around securing member 3202.

In this embodiment, securing member 3202 is associated with securing hole 3205 of implant 3200. Securing hole 3205 is configured with locking recess set 3280. In this embodiment, locking recess set 3280 includes eight locking recesses. Locking recess set 3280 preferably includes first locking recess 3281, second locking recess 3282, third locking recess 3283, fourth locking recess 3284, fifth locking recess 3285, sixth locking recess 3286, seventh locking recess 3287 and eighth locking recess 3288. Furthermore, locking recess set 3280 comprises locking recesses that are regularly spaced around securing hole 3205.

Preferably, the locking recesses of locking recess set 3280 are configured to receive the locking protrusions of locking protrusion set 3270 in order to prevent unwanted twisting of securing member 3202 within securing hole 3205. This arrangement allows securing member 3202 to be fastened until the protrusions of locking protrusion set 3270 are engaged in the closest locking recess of locking recess set 3280. By having a greater number of locking recesses than locking protrusions, greater control can be achieved in the fastening of securing member 3202 to implant 3200.

Figure 33:
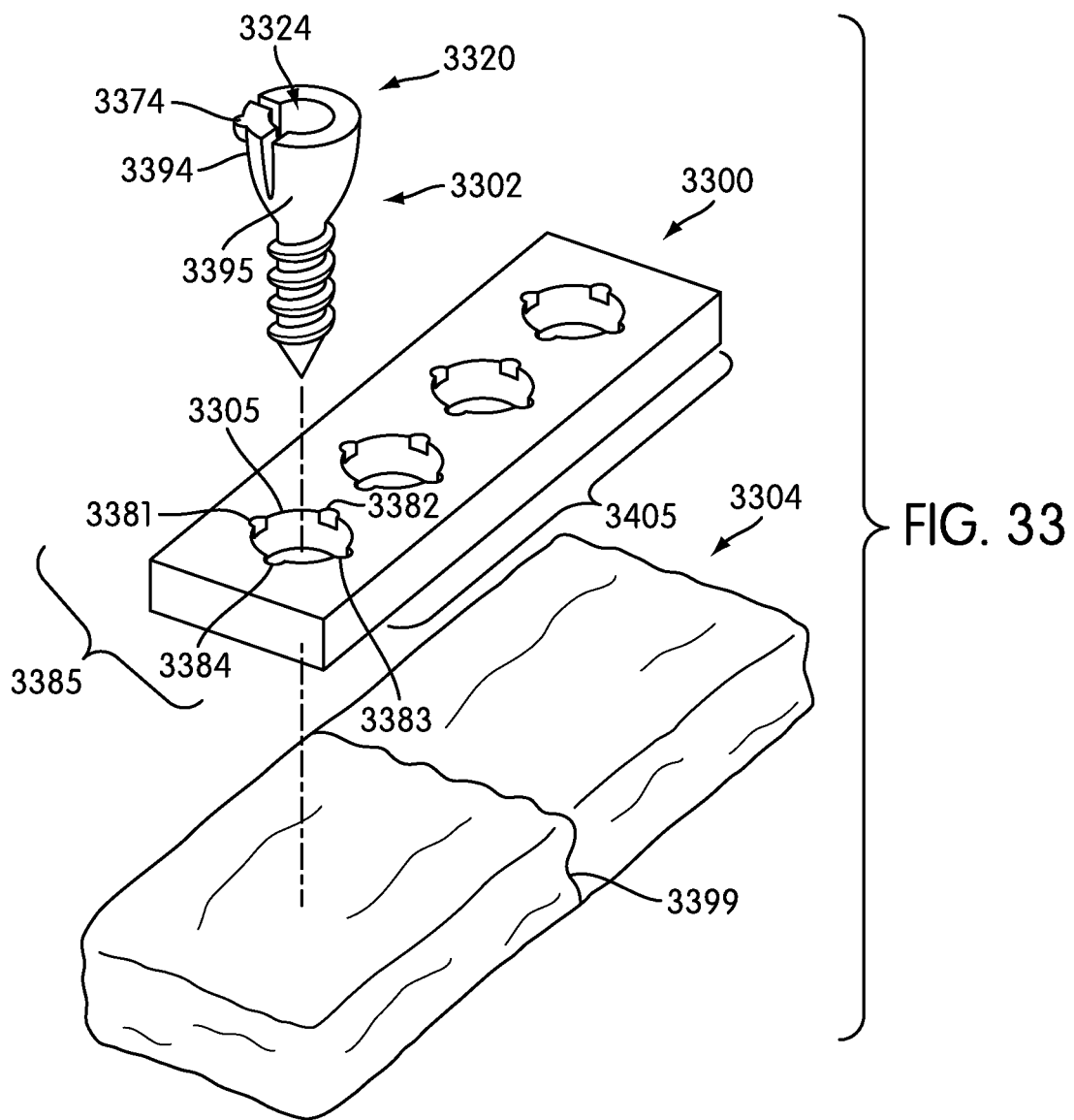
FIG. 33 is an exploded isometric view of an exemplary embodiment of a securing member with a single deflecting portion that is configured to secure an implant to a bone.
Figure 34:
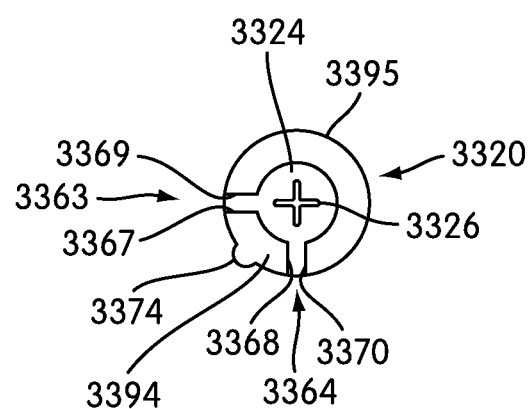
FIG. 34 is a top view of an exemplary embodiment of a securing member with a single deflecting portion.

FIGS. 33-34 illustrate an exemplary embodiment of securing member 3302 configured with a single deflecting portion 3394 rather than multiple deflecting portions as previously described. In this embodiment, securing member 3302 may fasten implant 3300 to bone 3304 to reinforce fracture 3399. To fasten to bone 3304, implant 3300 includes securing hole set 3405 comprising four securing holes. For purposes of clarity, securing member 3302 may be associated with securing hole 3305 of securing hole set 3405. Additional securing members may be associated with the remaining securing holes of securing hole set 3405.

In this embodiment, drive receiving portion 3320 is configured with a single deflecting portion 3394. As with previous embodiments, drive receiving portion 3320 of securing member 3302 includes central cavity 3324. Central cavity 3324 also includes drive receiving surface 3326 as seen in FIG. 34. Drive receiving surface 3326 may engage a fastening tool to fasten securing member 3302 to implant 3300 and bone 3304. As a fastening tool fastens securing member 3302, deflecting portion 3394 preferably undergoes inward deflection while drive receiving portion 3320 comes into contact with inner portions of securing hole 3305.

In this exemplary embodiment, drive receiving portion 3320 has a first slot 3363 and a second slot 3364 formed therein on opposite sides of deflecting portion 3394, which separates it from remaining support portion 3395 of drive receiving portion 3320. Deflecting portion 3394 can have a first edge 3367 along one side of first slot 3363 and a second edge 3368 along one side of second slot 3364, which are opposed in their slots by third edge 3369 and fourth edge 3370 respectively of support portion 3395. These straightened edges may provide for smooth engagement between deflecting portion 3394 and support portion 3395 during inward deflection.

Preferably, deflecting portion 3394 may also include one or more locking protrusions 3374 in order to lock securing member 3302 in place following insertion. Generally, locking protrusion 3374 may include any particular shape that allows locking protrusion 3374 to lock into corresponding recesses within securing hole 3305. In particular, securing hole 3305 can include first locking recess 3381, second locking recess 3382, third locking recess 3383 and fourth locking recess 3384 referred to collectively as recess set 3385. With this arrangement, securing member 3302 may be securely fastened within securing hole 3305 by the inward deflection of deflecting portion 3394 and the alignment of locking protrusion 3374 with one of the locking recesses in recess set 3385. Further, this arrangement of locking recesses, which can be disposed generally evenly around the perimeter of securing hole 3305 and can have more locking recesses than locking protrusions, can allow flexibility during insertion. In particular, such an arrangement can permit the insertion of securing member 3302 into bone 3304 to be stopped more readily by the surgeon when securing member 3302 has penetrated a desired depth into bone 3304. It can do so by readily engaging an adjacent one of the multiple locking recesses in recess set 3385 when securing member 3302 has penetrated a desired

What is claimed is:

1. An implant system, comprising:
   a securing member configured to implant into a bone;
   a plate configured to associate with the bone, the plate including a securing hole for receiving the securing member;
   the plate further including a first side and a second side, the second side being oriented to face the bone and the first side being oriented to face away from the bone;
   the securing member comprising a threaded portion disposed on a distal portion of the securing member and a drive receiving portion disposed on a proximal portion of the securing member;
   the drive receiving portion having at least one deflecting portion;
   the at least one deflecting portion including a locking protrusion;
   the locking protrusion comprising a rib extending from an uppermost surface of the drive receiving portion to a lowermost surface of the drive receiving portion;
   the locking protrusion extending along a longitudinal axis of the securing member;
   the securing hole of the plate defined by a sidewall that includes a locking channel configured to receive the locking protrusion;
   wherein the locking channel extends along the sidewall the entire length from the first side of the plate to the second side of the plate such that the locking channel is capable of receiving the locking protrusion of the securing member when the securing hole receives the securing member;
   wherein the locking protrusion extends along the entire surface of the locking channel; and
   wherein the at least one deflecting portion is configured to undergo inward deflection during insertion through the securing hole in the plate and wherein the at least one deflecting portion remains deflected following insertion.

2. The implant system according to claim 1, wherein the drive receiving portion has a first diameter prior to insertion and a second diameter following insertion, and wherein the second diameter is less than the first diameter.

3. The implant system according to claim 2, wherein the drive receiving portion has a third diameter during insertion and wherein the second diameter is different than the third diameter.

4. The implant system according to claim 1, wherein the at least one deflecting portion is disposed radially outwards on the drive receiving portion.

5. The implant system according to claim 1, wherein the at least one deflecting portion has a shape selected from the group consisting essentially of complementary nesting shapes, segmented annulus shapes, circular shapes, rectangular shapes, triangular shapes, regular polygonal shapes and irregular shapes.

6. An implant system, comprising:
   a securing member configured to implant into a bone;
   a plate configured to associate with the bone, the plate including a securing hole for receiving the securing member;
   the plate further including a first side and a second side, the second side being oriented to face the bone and the first side being oriented to face away from the bone;
   the securing member comprising a threaded portion disposed on a distal portion of the securing member and a drive receiving portion disposed on a proximal portion of the securing member;
   the drive receiving portion having a first deflecting portion and a second deflecting portion;
   the first deflecting portion including a locking protrusion;
   the locking protrusion comprising a rib extending from an uppermost surface of the drive receiving portion to a lowermost surface of the drive receiving portion;
   the locking protrusion extending along a longitudinal axis of the securing member;
   the securing hole of the plate defined by a sidewall that includes a locking channel configured to receive the locking protrusion;
   wherein the locking channel extends along the sidewall the entire length from the first side of the plate to the second side of the plate such that the locking channel is capable of receiving the locking protrusion of the securing member when the securing hole receives the securing member; and
   wherein the locking protrusion extends along the entire surface of the locking channel.

7. The implant system according to claim 6, wherein the drive receiving portion of the securing member has a proximal side and a distal side that is opposite to the proximal side and that is adjacent to the distal portion of the securing member, and wherein the locking protrusion decreases in size as the locking protrusion extends from the proximal side of the drive receiving portion to the distal side of the drive receiving portion.

8. The implant system according to claim 7, wherein the locking channel decreases in size as the locking channel extends from the first side of the plate to the second side of the plate.

9. The implant system according to claim 6, wherein the locking channel is tapered such that the locking channel has a widened portion and a narrow portion.

10. The implant system according to claim 9, wherein the widened portion is separated from the narrow portion by a circumferential distance that is approximately one quarter of the circumference of the securing hole.

11. The implant system according to claim 6, wherein the second deflecting portion includes a second locking protrusion configured to engage a second channel of the securing hole, wherein the second locking protrusion extends from the proximal side of the drive receiving portion to the distal side of the drive receiving portion, and wherein the second channel extends from the first side of the plate to the second side of the plate.

12. The implant system according to claim 6, the locking protrusion comprising a first locking protrusion and the locking channel comprising a first locking channel;
   the second deflecting portion including a second locking protrusion;
   the second locking protrusion comprising a second rib extending from an uppermost surface of the drive receiving portion to a lowermost surface of the drive receiving portion;
   the second locking protrusion extending along the longitudinal axis of the securing member;

the sidewall of the securing hole including a second locking channel configured to receive the second locking protrusion;

the second locking channel extending along the sidewall the entire length from the first side of the plate to the second side of the plate such that the second locking channel is capable of receiving the second locking protrusion of the securing member when the securing hole receives the securing member and when the first locking channel receives the first locking protrusion; and the second locking protrusion extending along the entire surface of the second locking channel.

13. An implant system, comprising:

a securing member configured to implant into a bone;

a plate configured to associate with the bone, the plate including a securing hole for receiving the securing member;

the plate further including a first side and a second side, the second side being oriented to face the bone and the first side being oriented to face away from the bone;

the securing member comprising a threaded portion disposed on a distal portion of the securing member and a drive receiving portion disposed on a proximal portion of the securing member;

the drive receiving portion having a first deflecting portion and a second deflecting portion;

the first deflecting portion including a locking protrusion;

wherein the drive receiving portion of the securing member has a proximal side and a distal side that is opposite to the proximal side and that is adjacent to the distal portion of the securing member, and wherein the locking protrusion comprises a rib that extends from an uppermost surface of the proximal side of the drive receiving portion to a lowermost surface of the distal side of the drive receiving portion;

the locking protrusion extending along a longitudinal axis of the securing member;

the securing hole of the plate defined by a sidewall that includes a locking channel configured to receive the locking protrusion;

wherein the locking channel extends along the sidewall the entire length from the first side of the plate to the second side of the plate such that the locking channel is capable of receiving the locking protrusion of the securing member when the securing hole receives the securing member; and wherein the locking protrusion extends along the entire surface of the locking channel.

14. The implant system according to claim 13, wherein the securing hole is generally circular.

15. The implant system according to claim 13, wherein the securing hole is generally oblong to allow for pivoting of the securing member.

16. The implant system according to claim 15, wherein the securing hole has a first diameter that is less than a second diameter of the drive receiving portion, wherein the securing hole includes a major axis and a minor axis, wherein the major axis is generally longer than the minor axis, and wherein the width of the minor axis is less than the second diameter of the drive receiving portion.

17. The implant system according to claim 16, wherein the securing member is configured to pivot in a direction generally along the major axis.

18. The implant system according to claim 13, wherein the drive receiving portion of the securing member has a curved outer surface along which the locking protrusion extends;

wherein the securing hole has a curved inner surface along which the locking channel extends;

wherein the curved inner surface of the securing hole is complementary to the curved outer surface of the drive receiving portion of the securing member such that an outer surface of the locking channel is complementary to an inner surface of the locking protrusion.

19. The implant system according to claim 13, wherein the first deflecting portion includes at least two locking protrusions.

20. The implant system according to claim 19, wherein the plate includes at least two locking channels that are configured to receive the at least two locking protrusions.

21. The implant system according to claim 13, wherein the first deflecting portion and the second deflecting portion are configured to deflect inwards during implantation of the securing member and wherein the first deflecting portion and the second deflecting portion are configured to return to a non-deflected state following implantation of the securing member.

22. The implant system according to claim 21, wherein the securing hole has a first diameter that is similar to a second diameter of the drive receiving portion.

\* \* \* \* \*